United States Patent
Bourne et al.

(10) Patent No.: US 10,195,409 B2
(45) Date of Patent: Feb. 5, 2019

(54) MULTIPLE IMPACT MICROPROJECTION APPLICATORS AND METHODS OF USE

(71) Applicant: Corium International, Inc., Menlo Park, CA (US)

(72) Inventors: Doug Bourne, Campbell, CA (US); Ashutosh Shastry, Santa Clara, CA (US); Anthony Le, San Jose, CA (US); Parminder Singh, Union City, CA (US)

(73) Assignee: Corium International, Inc., Menlo Park, CA (US)

( * ) Notice: Subject to any disclaimer, the term of this patent is extended or adjusted under 35 U.S.C. 154(b) by 872 days.

(21) Appl. No.: 14/203,378

(22) Filed: Mar. 10, 2014

(65) Prior Publication Data
US 2014/0276366 A1 Sep. 18, 2014

Related U.S. Application Data
(60) Provisional application No. 61/801,904, filed on Mar. 15, 2013.

(51) Int. Cl.
  *A61M 37/00* (2006.01)
  *A61M 5/158* (2006.01)

(52) U.S. Cl.
  CPC ........ *A61M 37/0015* (2013.01); *A61M 5/158* (2013.01); *A61M 37/0092* (2013.01); *A61M 2005/1585* (2013.01); *A61M 2037/0023* (2013.01); *A61M 2037/0061* (2013.01)

(58) Field of Classification Search
  CPC .. A61M 2037/0023; A61M 2037/0061; A61M 37/0015; A61M 37/0092; A61M 2005/1585; A61M 5/158
  See application file for complete search history.

(56) References Cited

U.S. PATENT DOCUMENTS

| | | | |
|---|---|---|---|
| 1,554,510 | A | 9/1925 | Kirby |
| 1,770,632 | A | 7/1930 | Smith |
| 2,046,240 | A | 6/1936 | Bayley |
| 2,434,407 | A | 1/1948 | George |
| 3,675,766 | A | 7/1972 | Rosenthal |
| 3,704,194 | A | 11/1972 | Name |
| 3,814,097 | A | 6/1974 | Ganderton et al. |
| 3,873,255 | A | 3/1975 | Kalwaites |
| 3,918,449 | A | 11/1975 | Pistor |
| 3,964,482 | A | 6/1976 | Gerstel et al. |

(Continued)

FOREIGN PATENT DOCUMENTS

| | | |
|---|---|---|
| CA | 2205444 | 6/1996 |
| CA | 2376285 | 12/2000 |

(Continued)

OTHER PUBLICATIONS

Avcin et al., "Subcutaneous nodule after vaccination with an aluminum-containing vaccine", Acta Dermatoven, APA, vol. 17, No. 4, pp. 182-184 (2008).

(Continued)

*Primary Examiner* — Brandy S Lee
(74) *Attorney, Agent, or Firm* — McDermott Will & Emery LLP

(57) ABSTRACT

Applicators for a microprojection array capable of multiple impacts and methods of using the applicators are described.

24 Claims, 4 Drawing Sheets

(56) References Cited

U.S. PATENT DOCUMENTS

| | | |
|---|---|---|
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,660,721 A | 4/1987 | Mykleby |
| 4,695,422 A | 9/1987 | Curro et al. |
| 4,743,234 A | 5/1988 | Leopoldi et al. |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,996,159 A | 2/1991 | Glaser |
| 5,051,259 A | 9/1991 | Olsen et al. |
| 5,061,258 A | 10/1991 | Martz |
| 5,134,079 A | 7/1992 | Cusack et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,163,918 A | 11/1992 | Righi et al. |
| 5,190,558 A | 3/1993 | Matsushita et al. |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabenau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,287 A | 6/1996 | Miskinyar |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,569,469 A | 10/1996 | Lovrechich |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Eriksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,868,244 A | 2/1999 | Ivanov et al. |
| 5,873,849 A | 2/1999 | Bernard |
| 5,879,326 A | 3/1999 | Godshall et al. |
| 5,900,252 A | 5/1999 | Calanchi et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,080,172 A | 6/2000 | Fujiwara et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,248,120 B1 | 6/2001 | Wyszogrodzki |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kleiner et al. |
| 6,379,324 B1 | 4/2002 | Garstein et al. |
| 6,440,096 B1 | 8/2002 | Lastovich et al. |

(56) References Cited

U.S. PATENT DOCUMENTS

| | | |
|---|---|---|
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,485,470 B2 | 11/2002 | Hostettler et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,512,626 B1 | 1/2003 | Schmidt |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whiston |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 6,991,809 B2 | 1/2006 | Anderson |
| 7,011,844 B2 | 3/2006 | Gale et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,128,730 B2 | 10/2006 | Marano-Ford et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Gartstein et al. |
| 7,611,481 B2 | 11/2009 | Cleary et al. |
| 7,658,728 B2 | 2/2010 | Yuzhakov |
| 7,678,777 B2 | 3/2010 | Yasuda et al. |
| 7,763,203 B2 | 7/2010 | Arias et al. |
| 7,785,301 B2 | 8/2010 | Yuzhakov |
| 7,789,733 B2 | 9/2010 | Sugimura |
| 7,798,987 B2 | 9/2010 | Trautman et al. |
| 7,828,827 B2 | 11/2010 | Gartstein et al. |
| 7,846,488 B2 | 12/2010 | Johnson |
| 7,914,480 B2 | 3/2011 | Cleary et al. |
| 8,057,842 B2 | 11/2011 | Choi et al. |
| 8,062,573 B2 | 11/2011 | Kwon |
| 8,216,190 B2 | 7/2012 | Gartstein et al. |
| 8,267,889 B2 | 9/2012 | Cantor et al. |
| 8,366,677 B2 | 2/2013 | Kaspar et al. |
| 8,696,638 B2 | 4/2014 | Terahara et al. |
| 8,702,726 B2 | 4/2014 | Gartstein et al. |
| 8,734,697 B2 | 5/2014 | Chen et al. |
| 8,747,362 B2 | 6/2014 | Terahara |
| 8,771,781 B2 | 7/2014 | Tokumoto et al. |
| 8,821,446 B2 | 9/2014 | Trautman et al. |
| 8,834,423 B2 | 9/2014 | Falo, Jr. et al. |
| 8,900,180 B2 | 12/2014 | Wolter et al. |
| 8,911,749 B2 | 12/2014 | Ghartey-Tagoe et al. |
| 9,114,238 B2 | 8/2015 | Singh et al. |
| 9,220,678 B2 | 12/2015 | Kendall et al. |
| 9,452,280 B2 | 9/2016 | Singh et al. |
| 9,498,524 B2 | 11/2016 | Ghartey-Tagoe et al. |
| 9,687,640 B2 | 6/2017 | Trautman et al. |
| 9,687,641 B2 | 6/2017 | Singh et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0123675 A1 | 9/2002 | Trautman et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0188310 A1 | 12/2002 | Seward et al. |
| 2002/0193729 A1 | 12/2002 | Cormier et al. |
| 2002/0193819 A1 | 12/2002 | Porter et al. |
| 2003/0083645 A1* | 5/2003 | Angel ............... A61M 5/14248 604/890.1 |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0062813 A1 | 4/2004 | Cormier et al. |
| 2004/0087893 A1* | 5/2004 | Kwon ................. A61B 17/205 604/46 |
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |

(56) References Cited

U.S. PATENT DOCUMENTS

| | | |
|---|---|---|
| 2005/0065463 A1 | 3/2005 | Tobinga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2005/0256045 A1 | 11/2005 | Ameri et al. |
| 2005/0261631 A1 | 11/2005 | Clarke et al. |
| 2006/0024358 A1 | 2/2006 | Santini et al. |
| 2006/0067943 A1 | 3/2006 | Maa et al. |
| 2006/0076718 A1 | 4/2006 | Sherman et al. |
| 2006/0095061 A1 | 5/2006 | Trautman et al. |
| 2006/0108914 A1 | 5/2006 | Young |
| 2006/0129174 A1 | 6/2006 | Gartstein et al. |
| 2006/0134188 A1 | 6/2006 | Podhaisky et al. |
| 2006/0149297 A1 | 7/2006 | Sherman et al. |
| 2006/0253079 A1* | 11/2006 | McDonough ...... A61M 37/0015 604/173 |
| 2007/0027427 A1 | 2/2007 | Trautman et al. |
| 2007/0191761 A1 | 8/2007 | Boone et al. |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0114298 A1 | 5/2008 | Cantor et al. |
| 2008/0125743 A1 | 5/2008 | Yuzhakov |
| 2008/0183144 A1 | 7/2008 | Trautman et al. |
| 2008/0188771 A1* | 8/2008 | Boecker ............... A61B 5/1411 600/583 |
| 2008/0195035 A1 | 8/2008 | Frederickson et al. |
| 2008/0208134 A1 | 8/2008 | Tomono |
| 2008/0208146 A1 | 8/2008 | Brandwein et al. |
| 2008/0214987 A1 | 9/2008 | Xu |
| 2008/0221532 A1 | 9/2008 | Ogawa |
| 2008/0269685 A1 | 10/2008 | Singh et al. |
| 2009/0017210 A1 | 1/2009 | Andrianov et al. |
| 2009/0035446 A1 | 2/2009 | Kwon |
| 2009/0041810 A1 | 2/2009 | Andrianov et al. |
| 2009/0043279 A1 | 2/2009 | Kaspar et al. |
| 2009/0155330 A1 | 6/2009 | Ghartey-Tagoe et al. |
| 2009/0182306 A1 | 7/2009 | Lee et al. |
| 2009/0216215 A1 | 8/2009 | Thalmann et al. |
| 2010/0028390 A1 | 2/2010 | Cleary et al. |
| 2010/0200494 A1 | 8/2010 | Storer |
| 2010/0228203 A1 | 9/2010 | Quan et al. |
| 2010/0247698 A1 | 9/2010 | Zhang et al. |
| 2011/0006458 A1 | 1/2011 | Sagi et al. |
| 2011/0028905 A1 | 2/2011 | Takada |
| 2011/0046638 A1 | 2/2011 | Gartstein et al. |
| 2011/0059150 A1 | 3/2011 | Kendall et al. |
| 2011/0098651 A1 | 4/2011 | Falo et al. |
| 2011/0121486 A1 | 5/2011 | Oh et al. |
| 2011/0160069 A1 | 6/2011 | Carrie et al. |
| 2011/0177139 A1 | 7/2011 | Hyungil et al. |
| 2011/0276027 A1 | 11/2011 | Trautman et al. |
| 2011/0276028 A1 | 11/2011 | Singh et al. |
| 2011/0280800 A1 | 11/2011 | Wu et al. |
| 2011/0288484 A1 | 11/2011 | Kendall et al. |
| 2011/0288485 A1 | 11/2011 | Tokumoto et al. |
| 2011/0306853 A1* | 12/2011 | Black ................... A61B 5/1468 600/309 |
| 2012/0052120 A1 | 3/2012 | Castor |
| 2012/0123387 A1* | 5/2012 | Gonzalez .......... A61M 37/0015 604/506 |
| 2012/0126297 A1 | 5/2012 | Brancazio |
| 2012/0130306 A1 | 5/2012 | Terahara et al. |
| 2012/0150023 A1 | 6/2012 | Kaspar et al. |
| 2012/0184906 A1 | 7/2012 | McAllister |
| 2012/0330250 A1* | 12/2012 | Kuwahara ......... A61M 37/0015 604/272 |
| 2013/0131598 A1 | 5/2013 | Trautman et al. |
| 2013/0287832 A1 | 10/2013 | O'Hagan et al. |
| 2013/0292868 A1 | 11/2013 | Singh et al. |
| 2013/0292886 A1 | 11/2013 | Sagi et al. |
| 2013/0303502 A1 | 11/2013 | Cavanagh et al. |
| 2014/0148846 A1 | 5/2014 | Pereira et al. |
| 2014/0180201 A1 | 6/2014 | Ding et al. |
| 2014/0248312 A1 | 9/2014 | Rappuoli et al. |
| 2014/0257188 A1 | 9/2014 | Kendall et al. |
| 2014/0272101 A1 | 9/2014 | Chen et al. |
| 2014/0276366 A1 | 9/2014 | Bourne et al. |
| 2014/0276378 A1 | 9/2014 | Chen et al. |
| 2014/0276474 A1 | 9/2014 | Ding et al. |
| 2014/0276580 A1 | 9/2014 | Le et al. |
| 2014/0276589 A1 | 9/2014 | Bayramov et al. |
| 2015/0079133 A1 | 3/2015 | Ghartey-Tagoe et al. |
| 2015/0238413 A1 | 8/2015 | Mochizuki et al. |
| 2015/0297878 A1 | 10/2015 | Singh et al. |
| 2016/0058992 A1 | 3/2016 | Chen et al. |
| 2016/0067176 A1 | 3/2016 | Ding et al. |
| 2016/0135895 A1 | 5/2016 | Faasse et al. |
| 2016/0175572 A1 | 6/2016 | Crowley et al. |
| 2016/0374939 A1 | 12/2016 | Shastry et al. |
| 2017/0281535 A1 | 10/2017 | Singh et al. |
| 2017/0361079 A1 | 12/2017 | Trautman et al. |

FOREIGN PATENT DOCUMENTS

| | | |
|---|---|---|
| CA | 2316534 | 3/2001 |
| CA | 2422907 | 4/2002 |
| CA | 2889500 A1 | 5/2014 |
| CN | 102000020 A | 6/2011 |
| CN | 102580232 A | 7/2012 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0305123 A1 | 3/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 A1 | 3/2001 |
| EP | 1174078 | 1/2002 |
| EP | 2283809 A1 | 2/2011 |
| EP | 2399624 A1 | 12/2011 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |

(56) References Cited

FOREIGN PATENT DOCUMENTS

| | | |
|---|---|---|
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-000728 A | 1/2002 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-534881 | 11/2003 |
| JP | 2004-065775 A | 3/2004 |
| JP | 2007-190112 A | 1/2006 |
| JP | 2006/271781 A | 10/2006 |
| JP | 2006-341089 A | 12/2006 |
| JP | 2007-130030 A | 5/2007 |
| JP | 2007-536988 A | 12/2007 |
| JP | 2008-006178 A | 1/2008 |
| JP | 2008-074763 A | 4/2008 |
| JP | 2008-194288 A | 8/2008 |
| JP | 2009-082206 A | 4/2009 |
| JP | 2009-082207 A | 4/2009 |
| JP | 2009-201956 A | 9/2009 |
| JP | 2010-233673 A | 10/2010 |
| JP | 2010-233674 A | 10/2010 |
| KR | 20100064669 A | 6/2010 |
| RU | 2414255 C1 | 3/2011 |
| SU | 1641346 | 4/1991 |
| SU | 1667864 | 8/1991 |
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 4/1996 |
| WO | WO 1996/017648 | 6/1996 |
| WO | WO 1996/037155 | 11/1996 |
| WO | WO 1996/037256 | 11/1996 |
| WO | WO 1997/003629 | 2/1997 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999/029365 | 6/1999 |
| WO | WO 1999/049874 A1 | 10/1999 |
| WO | WO 1999/061888 | 12/1999 |
| WO | WO 1999/064580 | 12/1999 |
| WO | WO 2000/005166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/008242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030301 A1 | 4/2002 |
| WO | WO 2002/032331 | 4/2002 |
| WO | WO 2002/032480 | 4/2002 |
| WO | WO 2002/062202 | 8/2002 |
| WO | WO 2002/064193 A2 | 8/2002 |
| WO | WO 2002/072189 | 9/2002 |
| WO | WO 2002/085446 A2 | 10/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000389 A2 | 12/2003 |
| WO | WO 2004/009172 A1 | 1/2004 |
| WO | WO 2004/024224 A1 | 3/2004 |
| WO | WO 2004/030649 A2 | 4/2004 |
| WO | WO 2004/076339 | 9/2004 |
| WO | WO 2004/105729 A2 | 12/2004 |
| WO | WO 2004/110717 | 12/2004 |
| WO | WO 2005/002453 A1 | 1/2005 |
| WO | WO 2005/046769 A1 | 5/2005 |
| WO | WO 2005/065765 A1 | 7/2005 |
| WO | WO 2005/082596 A1 | 9/2005 |
| WO | WO 2005/089857 A1 | 9/2005 |
| WO | WO 2005/094526 | 10/2005 |
| WO | WO 2005/099751 A2 | 10/2005 |
| WO | WO 2005/112984 A2 | 12/2005 |
| WO | WO 2006/020842 | 2/2006 |
| WO | WO 2006/055795 | 5/2006 |
| WO | WO 2006/062848 A1 | 6/2006 |
| WO | WO 2006/086742 A2 | 8/2006 |
| WO | WO 2006/101459 A1 | 9/2006 |
| WO | WO 2007/002521 A2 | 1/2007 |
| WO | WO 2007/002522 A1 | 1/2007 |
| WO | WO 2007/002523 | 1/2007 |
| WO | WO 2007/012114 A1 | 2/2007 |
| WO | WO 2007/030477 A2 | 3/2007 |
| WO | WO 2007/061964 A1 | 5/2007 |
| WO | WO 2007/061972 A2 | 5/2007 |
| WO | WO 2007/075806 A2 | 7/2007 |
| WO | WO 2007/081430 A2 | 7/2007 |
| WO | WO 2007/124411 | 11/2007 |
| WO | WO 2008/011625 | 1/2008 |
| WO | WO 2008/015236 A1 | 2/2008 |
| WO | WO 2008/024141 A2 | 2/2008 |
| WO | WO 2008/091602 | 7/2008 |
| WO | WO 2008/130587 | 10/2008 |
| WO | WO 2008/139648 A1 | 11/2008 |
| WO | WO 2009/039013 A1 | 3/2009 |
| WO | WO 2009/048507 A1 | 4/2009 |
| WO | WO 2009/054988 A1 | 4/2009 |
| WO | WO 2009/142741 A1 | 11/2009 |
| WO | WO 2010/040271 A1 | 4/2010 |
| WO | WO 2010/124255 A2 | 10/2010 |
| WO | WO 2011/121023 A1 | 10/2011 |
| WO | WO 2011/140240 | 10/2011 |
| WO | WO 2011/140274 | 10/2011 |
| WO | WO 2012/054582 A2 | 4/2012 |
| WO | WO 2012/122163 A1 | 9/2012 |
| WO | WO 2012/127249 A1 | 9/2012 |
| WO | WO 2012/153266 A2 | 11/2012 |
| WO | WO 2013/172999 A1 | 11/2013 |
| WO | WO 2014/004301 A1 | 1/2014 |
| WO | WO 2014/077244 A1 | 5/2014 |
| WO | WO 2014/100750 A1 | 6/2014 |
| WO | WO 2014/144973 A1 | 9/2014 |
| WO | WO 2014/150069 A1 | 9/2014 |
| WO | WO 2014/150285 A2 | 9/2014 |
| WO | WO 2014/151654 A1 | 9/2014 |
| WO | WO 2014/164314 A1 | 10/2014 |
| WO | WO 2016/033540 A1 | 3/2016 |
| WO | WO 2016/036866 A1 | 3/2016 |
| WO | WO 2016/073908 A1 | 5/2016 |
| WO | WO 2017/004067 A1 | 1/2017 |

OTHER PUBLICATIONS

Corbett et al., "Skin vaccination against cervical cancer associated human papillomavirus with a novel micro-projection array in a mouse model", PLOS one, vol. 5, No. 10, pp. 1-9 (2010).

Database WPI / Thomson, Accession No. 2014-V89218, Gao et al., "Soluble microneedle patch useful for transdermal administration of vaccine, comprises water-soluble polymer material as matrix mate-

(56) References Cited

OTHER PUBLICATIONS rial and soluble microneedle main portion", Application No. CN104027324A, Tech Inst Phys. & Chem. Chinese Acad., 3 pages (2014).
Ghosh et al., "Influence of critical parameters of nanosuspension formulation on permeability of a poorly soluble drug through the skin—A case study", vol. 14, No. 3, pp. 1108-1117 (2013).
Guo et al., "Enhanced transcutaneous immunization via dissolving microneedie array loaded with liposome encapsulated antigen and adjuvant", Int. J. Pharm., vol. 447, No. 1-2, pp. 22-30 (2013).
Gupta, "Aluminum compounds as vaccine adjuvants", Adv. Drug Deliv. Rev., vol. 32, No. 3, pp. 155-172 (1998) Abstract Only.
Gupta and Rost, "Aluminum compounds as vaccine adjuvants", Vaccine adjuvants: Preparation Methods and Research Protocols, O'Hagan, ed., Humana Press, Inc., Totowa, New Jersey, Meth. Mol. Med., vol. 42, No. 4, No. 4, pp. 65-89 (2000).
International Search Report from International Patent Application No. PCT/US2014/022836 dated May 9, 2015.
International Search Report from International Patent Application No. PCT/US2015/047563 dated Nov. 20, 2015.
International Search Report from International Patent Application No. PCT/US2015/048161 dated Nov. 26, 2015.
Kuroda et al., "Particulate adjuvant and innate immunity: past achievements, present findings, and future prospects", Int. Rev. Immunol., vol. 32, No. 2, pp. 209-220 (2013).
Munks et al., "Aluminum adjuvants elicit fibrin-dependent extracellular traps in vivo", Blood, vol. 116, No. 24, pp. 5191-5199 (2010).
Petrovsky and Aguilar, "Vaccine adjuvants: current state and future trends", Immunol. Cell Biol., vol. 82, No. 5, pp. 488-496 (2004).
Pittman, "Aluminum-containing vaccine associated adverse events: role of route of administration and gender", Vaccine, vol. 20, pp. s48-s50 (2002).
Prausnitz, "Microneedle-based vaccines", Curr. Top. Microbiol. Immunol., vol. 333, pp. 369-393 (2009).
Sayers et al., "Vaxjo: A Web-Based Vaccine Adjuvant Database and Its Application for Analysis of Vaccine Adjuvants and Their Uses in Vaccine Development", J. Biomed. Biotechnol., vol. 2012, Article ID: 831486, 13 pages, doi:10.1155/2012/831486 (2011).
White et al., "Studies on antibody production. III. The alum granuloma", J. Exp. Med., vol. 102, No. 1, pp. 73-82 (1955).
International Search Report from International Patent Application No. PCT/US2015/059559 dated Jan. 21, 2016.
Keitel et al., "A randomized clinical trail of acellular pertussis vaccines in healthy adults: Dose-response comparisons of 5 vaccines and implications for booster immunization", J. Infect. Dis., vol. 180, pp. 397-403 (1999).
Lutrol F 68 NF, BASF Pharma Ingredients, accessed from the internet on Sep. 5, 2016 from http://www2.basf.us/Pharma/pdf/Lutrol_F_68.pdf.
Vitiello et al., "Development of a lipopeptide-based therapeutic vaccine to treat chronic HBV infection", J. Clin. Invest., vol. 95, pp. 341-349 (1995).
"Eudragit EPO Readymix—Taste masking and moisture protection have never been easier" Evonik Industries, Evonik industries AG, Pharma Polymers & Services. Nov. 2014.
International Search Report from International Patent Application No. PCT/US2014/022859 dated May 26, 2014.
International Search Report from International Patent Application No. PCT/US2014/021841 dated Aug. 11, 2014.
International Search Report from International Patent Application No. PCT/US2014/026179 dated Jul. 18, 2014.
International Search Report from International Patent Application No. PCT/US2014/029601 dated Jul. 1, 2014.
Chun, et al., "An array of hollow microcapilaries for the controlled injection of genetic materials into animal/plant cells." IEEE Workshop on Micro Electro Mechnical Systems, pp. 406-411, (1999).
"Extend", Merriam-Webster Online Dictionary, 6 pages. Downloaded on Sep. 7, 2010 from <http://www.merriam-webster.com/dictionary/extend>.

"Extend", Macmillan Online Dictionary, 5 pages. Downloaded on Sep. 7, 2010 from <http://www.macmillandictionary.com/dictionary/american/extend>.
Henry et al., "Micromachined microneedles for transdermal delivery of drugs", IEEE Workshop on Micro Electro Mechanical Systems, New York, NY, pp. 494-498, (1998).
Henry, et al., "Microfabricated microneedles: A novel approach to transdermal drug delivery", J. Pharmaceutical Science, vol. 87, No. 8, pp. 922-925, (1998).
"Heparin Pregnancy and Breast Feeding Warnings", Drugs.com, Accessed Oct. 8, 2009, <http://www.drugs.com/pregnancy/heparin.html>.
International Search Report from International Patent Application No. PCT/US2000/015612 dated Sep. 7, 2000.
International Search Report from International Patent Application No. PCT/US2000/015613 dated Sep. 6, 2000.
International Search Report from International Patent Application No. PCT/US2000/015614 dated Sep. 6, 2000.
International Search Report from International Patent Application No. PCT/US2001/031977 dated Apr. 29, 2002.
International Search Report from International Patent Application No. PCT/US2001/031978 dated Apr. 29, 2002.
International Search Report from International Patent Application No. PCT/US2002/014624 dated Sep. 3, 2002.
International Search Report from International Patent Application No. PCT/US2002/029228 dated Apr. 23, 2003.
International Search Report from International Patent Application No. PCT/US2002/029245 dated Dec. 27, 2002.
International Search Report from International Patent Application No. PCT/US2004/005382 dated Nov. 25, 2004.
International Search Report from International Patent Application No. PCT/US2004/017255 dated May 24, 2005.
International Search Report from International Patent Application No. PCT/US2005/009654 dated Jul. 3, 2008.
International Search Report from International Patent Application No. PCT/US2008/000824 dated Jul. 18, 2008.
International Search Report from International Patent Application No. PCT/US2008/004943 dated Jun. 9, 2009, application now published as International Publication No. WO2008/130587 Oct. 30, 2008.
International Search Report from International Patent Application No. PCT/US2008/011635 dated Dec. 19, 2008, application now published as International Publication No. WO2009/048607 on Apr. 16, 2009.
International Search Report from International Patent Application No. PCT/US2010/032299 dated Dec. 10, 2010, application now published as International Publication No. WO2010/124255 on Oct. 28, 2010.
International Search Report from International Patent Application No. PCT/US2013/077281 dated Mar. 4, 2013.
International Search Report from International Patent Application No. PCT/US2014/022087 dated May 23, 2014.
Matriano, et al., "Macroflux(R) microprojection array patch technology: A new and efficient approach for intracutaneous immunization", Pharm. Res., vol. 19, No. 1, pp. 63-70, (2002).
McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.
Mikszta, et al., "Improved genetic immunization via micromechanical disruption of skin-barrier function and targeted epidermal delivery", Nat. Med., vol. 8, No. 4, pp. 415-419, (2002).
Mikszta, et al., "Protective immunization against inhalation anthrax: A comparison of minimally invasive delivery platforms", J. Inf. Dis., vol. 191, No. 2, pp. 278-288, (2005).
Papautsky, et al., "Micromachined Pipette Arrays," MPA, Proceedings—19th International Conference—IEEE/EMBS, Chicago, IL, USA, pp. 2281-2284 (1997).
Park et al., "Biodegradable polymer microneedles: Fabrication, mechanics, and transdermal drug delivery", J. Contr. Rel., vol. 104, pp. 51-66 (2005).
Park, et al. "Polymer Microneedles for Controlled-Release Drug Delivery," Pharmaceutical Research, Kluwer Academic Publishers—Plenum Publishers, NE, vol. 23, No. 5, pp. 1008-1019 (2006).

(56) References Cited

OTHER PUBLICATIONS

Prausnitz, et al., "Transdermal transport efficiency during skin electroporation and iontophoresis", J. Contr. Release, vol. 38, pp. 205-217, (1996).
Prausnitz, "Transdermal delivery of macromolecules: Recent advances by modification of skin's barrier properties", ACS Symposium Series No. 675, *Therapeutic Protein and Peptide Formulation and Delivery*, American Chemical Soceity, Washington DC, Chapter 8, pp. 124-153, (1997).
Rydberg, et al., "Low-molecular-weight heparin preventing and treating DVT", Am. Fam. Physician, vol. 59, No. 6, pp. 1607-1612, (1999).
Sivamani, et al., "Microneedles and transdermal applications", Exp. Opin, Drug Del., vol. 4, No. 1, pp. 19-25, (2007).
Wouters, et al., "Microelectrochemical systems for drug delivery", Electrochimica Acta., vol. 42, pp. 3385-3390, (1997).
Xia, et al., "Soft Lithography", Agnew. Chem. Int. Ed, vol. 37, pp. 551-575, (1998).
Xia, et al., "Soft Lithography", Annu. Rev. Mater. Sci., vol. 28, pp. 153-184 (1998).
International Search Report from International Patent Application No. PCT/US2011/035221 dated Jan. 10, 2012, application now published as International Publication No. WO2011/140240 on Nov. 10, 2011.
International Search Report from International Patent Application No. PCT/US2016/039864 dated Sep. 23, 2016.
Makaida et al., "Poly lactic-co-glycolic acid (PLGA) as biodegradable controlled drug delivery carrier", Polymers (Basel), vol. 3, No. 3, pp. 1377-1397 (2011).
Julinova et al., "Initiating biodegradation of polyvinylpyrrolidone in aqueous aerobic environment", Proceedings of ECOpole, vol. 6, No. 1, pp. 121-127 (2012).
Kunduru et al., "Biodegradable polymers: Medical Applications", Encyclopedia of Polymer Science and Technology, pp. 1-22 (2016) DOI: 10.1002/0471440264.pst027.pub2.

\* cited by examiner

MULTIPLE IMPACT MICROPROJECTION APPLICATORS AND METHODS OF USE

CROSS-REFERENCE TO RELATED APPLICATIONS

This application claims the benefit of U.S. Provisional Application No. 61/801,904, filed Mar. 15, 2013, which is incorporated herein by reference in its entirety.

TECHNICAL FIELD

The subject matter described herein relates generally to a method and delivery system for drug delivery using microprojections, and more specifically to applicators for applying an array of microprojections that provide multiple impacts.

BACKGROUND

Arrays of microneedles were proposed as a way of administering drugs through the skin in the 1970s, for example in U.S. Pat. No. 3,964,482. Microneedle or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

In recent years it has become more feasible to manufacture microstructure arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use and maintaining it in controlled storage.

In addition to cost, integrity and sterility, a further issue with microneedle arrays is bioavailability of the active agent. An intravenous injection delivers a precise quantity of an active agent to the circulation. A subcutaneous or intramuscular injection delivers a precise quantity of an active agent into the tissue, but the quantity of active agent delivered to the circulation and the rate at which active ingredient is delivered are affected by the type of surrounding tissue, circulation, and possibly other factors. When a drug is delivered orally, the resulting blood levels may exhibit substantial variation among patients due to metabolism and other factors, but minimal therapeutic levels can be assured for most patients, for example, because the rate of metabolism has an upper limit and because there is long experience with the absorption of many drugs from oral formulations. When a drug is delivered to unmodified skin by a conventional transdermal patch, the bypassing of the hepatic circulation may lessen the effect of liver metabolism on bioavailability. On the other hand, with a conventional transdermal patch, differences in skin permeability are an additional factor leading to differences in bioavailability.

Microneedles manipulate the permeability of the skin with respect to the active agent. Variability in the permeability enhancement created by different applications of the microneedles will result in variations in the rate of transfer through the skin, the amount transferred through the skin and the bioavailability. Variability of skin permeability enhancement on the application of a microneedle array can result from application on different patients. Particular concern exists, of course, if the enhancement is small in particular patient populations so that the administration of the drug will not produce a therapeutically effective dosing (e.g., adequate blood levels) in those populations. Concern may arise also if the enhancement is sometimes undesirably small in a patient, even if at other times the enhancement is as expected in that patient, depending on details of how and where the microneedle array is applied.

A typical microneedle array comprises microneedles projecting from a base of a particular thickness, which may be of any shape, for example square, rectangular, triangular, or circular. The microneedles themselves may have a variety of shapes. While an array could be pressed by hand into skin, it has also been proposed to use a variety of devices to hold the microneedle array as it is being applied or to facilitate in one way or another the process of microneedle array application to the skin or other biological membrane. Such devices may broadly be referred to as "applicators." Applicators may for example reduce the variations in force, velocity, and skin tension that occur when a microneedle array is pressed by hand into the skin. Variations in force, velocity and skin tension can result in variations in permeability enhancement.

In some applications of microneedle arrays, they may be applied to the skin or other biological membrane in order to form microchannels and then are more or less immediately withdrawn. In other applications the microneedle array may be held in place for a longer period of time. The design of the applicator may naturally be influenced by how long the microneedles are expected to stay in place.

Applicators for microneedles comprising components which have two stable states have been described in U.S. Published Patent Application No. 2008/0183144. The existence of two stable states is a feature generally desired in an applicator because the energy difference between the two stable states can allow each use of the applicator to employ a fixed amount of energy in order to cause penetration, improving reproducibility.

One problem with prior art applicator designs is that the energy required to achieve penetration of the microneedles may result in a force to the patient's skin that is uncomfortable or painful. U.S. Pat. No. 6,743,211 describes vibrating the microneedles and/or the skin to enhance penetration. However, existing vibratory applicators are complex and expensive. They typically use a stand-alone piece of equipment, usually electronic in nature, to provide vibration. This separate, non-disposable vibratory machine is undesirable or even unobtainable in many areas. These devices are primarily used in a research setting due to their cost and complexity.

There is a need in the art for applicators and related devices suitable for use with microneedle arrays, for example, in order to assist in making the process of drug delivery more user friendly and uniform across patients and for different applications to the same patient. There is also a need for an applicator which has sufficient force to achieve desired penetration of a patient's skin with the microprojections without causing discomfort or pain.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, an applicator for a microprojection array is provided.

In one aspect, a method of delivering a therapeutic agent to a subject, comprises (i) applying to a skin site of a subject, an applicator comprising at least one plunger element, at least one microprojection retained on a distal surface of the plunger, and an actuator; (ii) actuating the actuator to convey an external force to the at least one plunger element such that an energy required for the at least one microprojection to penetrate the skin site is delivered in multiple, discrete quanta and/or impacts.

In an embodiment, a maximum strain and/or strain rate is not exceeded by any of the multiple, discrete quanta and/or impacts. In further embodiments, there is sufficient delay between impacts to allow a strain from a previous impact to dissipate.

In an embodiment, the at least one microstructure partially penetrates the skin site from a first impact, and the method further comprises detaching the at least one microstructure from the plunger distal end.

In embodiments, the multiple, discrete quanta and/or impacts are created by any one of or a combination of methods and devices including:

(a) the plunger comprises multiple energy-mass systems or the device includes a plurality of plunger elements each with an energy-mass system, each system having a different time constant so that the energy-mass systems progressively deploy;

(b) the applicator comprises a plurality of plunger elements and an asynchronous release mechanism such that the plunger elements are released at different time periods;

(c) the applicator comprises a plurality of plunger elements each comprising a dashpot element having a different damping coefficient;

(d) the applicator comprises a plurality of plunger elements, each having a different type of spring; and (e) the applicator further includes a vibration element.

In embodiments, each of the energy-mass systems has a progressively higher time constant such that the plunger elements impact the skin site in a defined sequence. In embodiments, the impacts are sequential. The timing of the impacts may be regular or irregular, which may depend on the time required for the strain from the prior impact to dissipate. In further embodiments, each energy-mass element includes a spring and a mass element. In additional embodiments, a delay in impact from the plunger elements may be modified by adjusting a spring constant of one or more springs in the energy-mass elements. In other embodiments a delay in impact from the plunger elements may be modified by adjusting a mass of the mass elements. In further embodiments, a cam or other mechanical feature may be used to build in delays in release in order to provide the asynchronous release. In additional embodiments, the different types of springs are selected from coiled springs, wave springs, and slotted springs. In further embodiments, an amplitude of the vibration element is controlled to limit an impact strain from one or more of the multiple, discrete quanta and/or impacts. In other embodiments, a frequency of the vibration element is controlled to limit an impact strain from one or more of the multiple, discrete quanta and/or impacts.

In another aspect, an applicator, comprises (i) at least a first plunger element comprising a first energy-mass system, the first plunger element having a first restrained position and a second extended position, the first plunger element comprising a distal end on which at least one microprojection can be retained; (ii) at least a second energy-mass system, wherein the first and second energy-mass systems each has a different time constant, and each energy-mass system has a first restrained position and a second extended position; and (iii) an actuating member that can convey an external force to at least the first plunger element to release the first plunger element from the first restrained position.

In embodiments, the applicator further includes at least one microstructure attached to a distal surface of the plunger element distal end.

In embodiments, the first and second energy-mass systems each includes a mass and an energy-storing element. In other embodiments the energy-storing elements are elastic energy elements. In further embodiments, the energy-storing elements are each selected from a compression spring, a coil spring, a wave spring, and a slotted spring. The energy-storing elements for the different energy-mass systems may be the same or different for each energy-mass system.

In embodiments, the energy-mass systems each have a time constant such that the energy-mass systems are released at the same time (simultaneously or near simultaneously) but deploy at different rates, and thus impact at different times. The applicator of any previous claim, wherein the first energy-mass system has a faster time constant than the second energy-mass system. In other embodiments, the mass of the first energy-mass system is different than the mass of the second energy-mass system. In further embodiments, the first energy-mass system has a stored energy sufficient to deploy the at least one microprojection at least partially into a subject's skin when the stored energy is released.

In embodiments, the applicator includes further energy-mass systems (third, fourth, fifth, or more) depending on the number of impacts desired. In an embodiment, the applicator includes a third energy-mass system, wherein the third energy-mass system has a different time constant than the first or second energy-mass systems. In other embodiments, the third energy-mass system has a slower time constant than the first or second energy-mass systems.

In embodiments, the applicator includes a housing where the first plunger element and actuating member are at least partially positioned in the housing. In other embodiments, the housing member includes a skin-contacting surface. In further embodiments, the skin-contacting surface further comprising an adhesive to secure the housing to a surface.

In embodiments, the at least one microprojection is a microprojection array comprising a plurality of microprojections. In other embodiments, at least some of the plurality of microprojections are dissolvable or erodible microprojections. In additional embodiments, at least some of the plurality of microprojections include at least one therapeutic agent. In yet other embodiments, the therapeutic agent is selected from a drug, a small molecule, a peptide or protein, or a vaccine. In other embodiments, at least a portion of the plurality of microprojections are detachable from the microprojection array.

In an embodiment, the first plunger element contacts a subject's skin with an energy of about 0.15-0.2 J.

In another embodiment, the applicator further includes a backing member positioned on the distal surface of the first plunger distal end, wherein the backing member comprises the at least one microprojection; the backing member being detachable from the first plunger element distal end. In other embodiments, the backing member comprises a support layer adjacent the distal surface of the first plunger element distal end and an adhesive layer, wherein the at least one microprojection is positioned distal to the adhesive layer. In additional embodiments, the at least one microprojection is a microprojection array positioned distal to the adhesive layer. In further embodiments, the adhesive layer at least partially surrounds the at least one microprojection.

In embodiments, the applicator further includes a damper positioned between at least one of the energy-storing elements and a proximal surface of the first plunger element distal end.

In another aspect, a method of delivering a therapeutic agent to a subject, comprises an applicator as described herein; actuating the actuating member to convey an external force to at least the first plunger element; releasing the first plunger element from the first restrained position to the second extended position to impact the subject's skin; and releasing the second energy-mass system from the first restrained position to the second extended position with a different time constant than the first plunger element; wherein the second energy mass system impacts a proximal surface of the first plunger distal end.

In an embodiment, the first plunger contacts the skin site of the subject with sufficient force for the at least one microprojection to at least partially penetrate the skin. In another embodiment, impact of the second energy-mass system on the first plunger element causes the at least one microprojection to penetrate the skin further upon impact.

In embodiments, the method further includes adhering the applicator to the subject's skin. In other embodiments, in the deployed position, the first plunger element has an equilibrium position such that the distal end of the plunger on which the at least one microprojection is retained is positioned below a surface of the skin. In further embodiments, the equilibrium position is about 0.03-0.2 inches below the surface of the skin of the subject.

In embodiments, the method further includes detaching a backing member such that the backing member and the at least one microprojection are retained on the subject's skin.

In embodiments, the therapeutic agent is selected from a drug, a small molecule, a peptide or protein, or a vaccine.

In another aspect, an applicator, comprises (a) a plunger element comprising at least a shaft and a distal end on which at least one microprojection can be retained; (b) at least one projection positioned on a proximal surface of the plunger distal end, the plunger having a first restrained position and a second extended position; (c) an actuating member that can convey an external force to the plunger element to release the plunger element from the first restrained position; (d) a linear energy-storing member positioned between the actuator and the plunger distal end, the linear energy-storing member having a first position and a second position, wherein the linear energy-storing member is effective to move the plunger from its first position to its second position as the linear energy-storing member moves from its first position to its second position; and (e) a torsional energy-mass system at least partially surrounding the plunger shaft and being positioned between the linear energy-storing member and the plunger distal end, wherein the torsional energy-mass system contacts the at least one projection as the torsional energy-mass system rotates about the plunger shaft.

In embodiments, the at least one projection comprises a plurality of projections spaced apart around the proximal surface of the plunger distal end.

In embodiments, the torsional energy-mass system contacts the at least one projection as the torsional energy-mass system rotates about the plunger shaft and pushes the plunger distal end downward. In further embodiments, the torsional energy-mass system includes a rod perpendicular to an axis of motion of the linear energy-storing member, wherein the rod contacts the at least one projection as the torsional energy-mass system rotates.

In embodiments, impact of the plunger distal end on a patient's skin releases the torsional spring-mass system.

In embodiments, each of the at least one protrusions are wedge shaped.

In embodiments, the energy-storing member is an elastic energy element. In other embodiments, the energy-storing elements are each selected from a compression spring, a coil spring, a wave spring, and a slotted spring. In further embodiments, the linear energy-storing member has a stored energy sufficient to deploy the at least one microprojection into a subject's skin when the stored energy is released.

In embodiments, the applicator includes a housing member at least partially housing the plunger member and actuating member. In other embodiments, the housing member includes a skin-contacting surface. In further embodiments, the skin-contacting surface further comprising an adhesive to secure the housing to a surface.

In embodiments, the at least one microprojection is a microprojection array comprising a plurality of microprojections. In other embodiments, at least some of the plurality of microprojections are dissolvable or erodible microprojections.

In embodiments, the plurality of microprojections includes at least one therapeutic agent. In further embodiments, the therapeutic agent is selected from a drug, a small molecule, a peptide or protein, or a vaccine.

In embodiments, at least a portion of the plurality of microprojections are detachable from the microprojection array.

In embodiments, the plunger element contacts a subject's skin with a force of about 0.15-0.2 J.

In embodiments, the applicator includes a backing member positioned on a bottom surface of the plunger distal end, wherein the backing member comprises the at least one microprojection; the backing member being detachable from the plunger distal end.

In embodiments, the backing member comprises a support layer adjacent the distal surface of the plunger distal end and an adhesive layer, wherein the at least one microprojection is positioned distal to the adhesive layer. In other embodiments the at least one microprojection is a microprojection array positioned distal to the adhesive layer. In further embodiments, the adhesive layer at least partially surrounds the at least one microprojection.

In embodiments, the applicator includes a damper positioned between the energy-storage devices and a proximal surface of the plunger distal end.

In another aspect, a method of delivering a therapeutic agent to a subject, comprises applying to a skin site of the subject, an applicator according to any one of the above embodiments, actuating the actuating member to convey an external force to the plunger element; releasing the plunger element from the first restrained position to the second extended position; rotating the torsional energy-mass system about the plunger shaft such that the system contacts the at least one projection on the plunger proximal surface and pushes it downward as the system rotates about the plunger shaft thereby to move the plunger distal end toward the skin site.

In embodiments, the plunger contacts the skin site of the subject in the extended position with sufficient force for the at least one microprojection to at least partially penetrate the skin. In other embodiments, rotation of the torsional energy-mass system causes the plunger to impact the patient's skin and causes the at least one microprojection to penetrate the skin further upon each impact. In further embodiments, the plunger distal end comprises a plurality of projections spaced apart around the proximal surface of the plunger distal end and rotation of the torsional energy-mass system causes the plunger to impact the patient's skin each time the system contacts one of the plurality of projections. In additional embodiments, the method includes adhering the applicator to the subject's skin.

In embodiments, in the deployed position, the plunger element has an equilibrium position such that the distal end of the plunger on which the at least one microprojection is retained is positioned below a surface of the skin. In other embodiments, the equilibrium position is about 0.03-0.2 inches below the surface of the skin of the subject.

In embodiments, the method further includes detaching a backing member such that the backing member and the at least one microprotrusion is retained on the subject's skin.

In embodiments, the therapeutic agent is selected from a drug, a small molecule, a peptide or protein, or a vaccine.

Additional embodiments of the present devices, apparatuses, methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present devices, apparatuses, and methods are set forth in the following description and claims, particularly when considered in conjunction with the accompanying examples and drawings.

Figure 1:
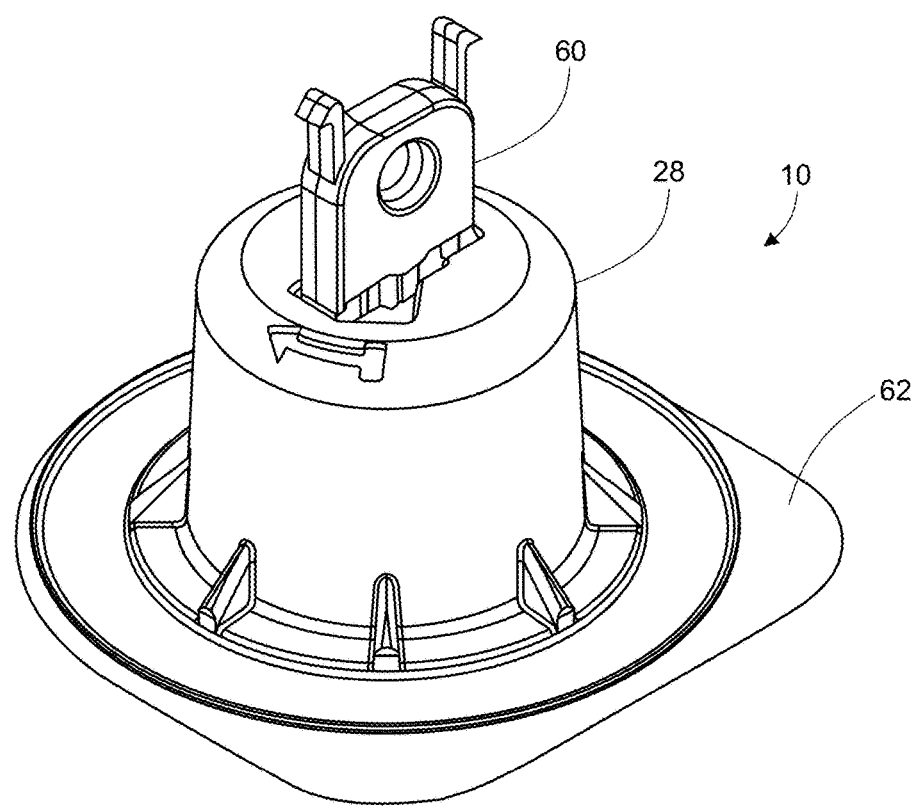
FIG. 1 is an illustration of a top perspective view of an exemplary applicator device.

It will be appreciated that the thicknesses and shapes for the various applicators and microstructure arrays have been exaggerated in the drawings to facilitate understanding of the device. The drawings are not necessarily "to scale."

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., $20^{th}$ Ed.; *Goodman & Gilman The Pharmacological Basis of Therapeutics*, J. Griffith Hardman, L. L. Limbird, A. Gilman, $10^{th}$ Ed.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

I. Definitions

As used in this specification, the singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

In describing and claiming the present invention, the following terminology will be used in accordance with the definitions described below.

In discussing the applicators and arrays, the term "downward" is sometimes used to describe the direction in which microprotrusions are pressed into skin, and "upward" to describe the opposite direction. However, those of skill in the art will understand that the applicators and arrays can be used where the microprotrusions are pressed into skin at an angle to the direction of the earth's gravity, or even in a direction contrary to that of the earth's gravity. In many applicators, the energy for pressing the microprotrusions is provided primarily by an energy-storage member and so efficiency is not much affected by the orientation of the skin relative to the earth's gravity.

The terms "microprotrusion", "microprojection", "microstructure" or "microneedle" are used interchangeably herein to refer to elements adapted to penetrate or pierce at least a portion of the stratum corneum or other biological membranes. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication No. U.S. 2008/0269685.

The term "microprotrusion array" for purposes herein is intended to denote a two-dimensional or a three-dimensional arrangement of microprotrusions, microprojections, microstructures, or microneedles. The arrangement may be regular according to a repeating geometric pattern or it may be irregular.

"Optional" or "optionally" means that the subsequently described circumstance may or may not occur, so that the description includes instances where the circumstance occurs and instances where it does not.

"Substantially" or "essentially" means nearly totally or completely, for instance, 80-85%, 80-90%, 80-95%, 85-90%, 85-95%, 90-95% or greater of some given quantity.

In this application reference is often made for convenience to "skin" as the biological membrane which the microneedles penetrate. It will be understood by persons of skill in the art that in most or all instances the same inventive principles apply to the use of microneedles to penetrate other biological membranes such as, for example, those which line the interior of the mouth or biological membranes which are exposed during surgery. In other embodiments, the inventive principles may apply to the use of microneedles for cell walls. For example, the microneedles described herein may be used to treat a condition of the skin where certain cells that present on the surface are targeted by the microneedles.

"Transdermal" refers to the delivery of an agent into and/or through the skin or for local and/or systemic therapy.

II. Microstructure Applicators

Before describing the present subject matter in detail, it is to be understood that this invention is not limited to specific materials or device structures, as such may vary. It is also to be understood that the terminology used herein is for the purpose of describing particular embodiments only, and is not intended to be limiting.

In general, the microstructure applicators described herein provide multiple, discrete impacts with a single applicator. These applicators provide improved microstructure penetration than achieved by a single impact. Further, the applicators provide an improved sensation to the subject by providing multiple impacts with less force than required for a single impact.

Further, the energy required for penetration by the microstructures is delivered in multiple discrete quanta/impacts. A maximum strain and/or strain rate that limits sensation from the impacts to an acceptable level is not exceeded by any of the individual impacts. Thus, sensation for the subject is limited and is independent of the total energy provided by the devices herein.

Preferably, there is sufficient delay between the discrete impacts to allow the strain from the previous impact to dissipate so that the sensation from the impacts does not accumulate.

There are several ways to provide multiple discrete impacts. Suitable devices include a device with multiple energy-mass systems, described further below; provide asynchronous release of multiple plunger elements; use dashpot elements with multiple plunger elements; use different springs to provide different expansion and therefore timed impacts; and use a vibrating element.

In one embodiment, the device includes a plurality of plunger elements where release of the plunger elements is timed to provide multiple impacts. In one embodiment, a cam is used to build a delay in release into the applicator.

In another element, dashpot elements are used to create a damping of plunger elements and thus modulate the dynamics of an energy-mass system.

In a further embodiment, the plunger elements use a spring for movement within the actuator and different spring types are used to provide for timed release of the plunger elements. Suitable springs include, but are not limited to, coiled springs, wave springs, slotted springs, etc.

In another embodiment, the device uses vibration to create multiple, discrete impacts without the need to detach the microstructure array from the plunger. Preferably, the vibration element or device is associated with the actuating element. In one embodiment, the amplitude of vibration is controlled to ensure the strain is limited. In a second embodiment, the frequency is selected such that strain rates are limited and there is sufficient recovery time allowed for sensation to the subject to be limited. It will be appreciated that these embodiments may be used in combination.

In embodiments, the strain and/or strain rate may be limited and/or adjusted to a specified strain and/or rate. In embodiments, the strain and/or strain rate are limited to below a level which causes discomfort and/or pain sensation for the subject.

In an embodiment, the applicators and methods provide for a strain that is between about 0.1-100. In other embodiments, the strain is between about 0.1-5, about 0.1-10, about 0.1-15, about 0.1-20, about 0.1-25, about 0.1-30, about 0.1-40, about 0.1-50, about 0.1-60, about 0.1-70, about 0.1-75, about 0.1-80, about 0.1-90, about 0.1-95, about 0.5-100, about 0.5-10, about 0.5-15, about 0.5-20, about 0.5-25, about 0.5-30, about 0.5-40, about 0.5-50, about 0.5-60, about 0.5-70, about 0.5-75, about 0.5-80, about 0.5-90, about 0.5-95, about 0.75-100, about 0.75-10, about 0.75-15, about 0.75-20, about 0.75-25, about 0.75-30, about 0.75-40, about 0.75-50, about 0.75-60, about 0.75-70, about 0.75-75, about 0.75-80, about 0.75-90, about 0.75-95, about 1-100, about 1-5, about 1-10, about 1-15, about 1-20, about 1-25, about 1-30, about 1-40, about 1-50, about 1-60, about 1-70, about 1-75, about 1-80, about 1-90, about 1-95, about 5-100, about 5-10, about 5-15, about 5-20, about 5-25, about 5-30, about 5-40, about 5-50, about 5-60, about 5-70, about 5-75, about 5-80, about 5-90, about 5-95, about 10-100, about 10-15, about 10-20, about 10-25, about 10-30, about 10-40, about 10-50, about 10-60, about 10-70, about 10-75, about 10-80, about 10-90, about 10-95, about 20-100, about 20-25, about 20-30, about 20-40, about 20-50, about 20-60, about 20-70, about 20-75, about 20-80, about 20-90, about 20-95, about 25-100, about 25-50, about 25-75, about 40-100, about 40-50, about 40-75, about 50-100, about 50-60, about 50-70, about 50-75, about 50-80, about 50-90, about 50-95, about 60-100, about 60-70, about 60-75, about 70-100, about 70-75, about 75-100, about 80-100, about 80-90, about 90-100, or about 95-100.

In an embodiment, the applicators and methods maintain a strain rate of between about $10^{-1}$-$10^8$ s$^{-1}$. In other embodiments, the strain rate for the applicators and methods is between about $10^{-1}$-$10^1$, about $10^{-1}$-$10^2$, about $10^{-1}$-$10^5$, about $10^{-1}$-$10^6$, about $10^{-1}$-$10^6$, about $10^1$-$10^8$, about $10^1$-$10^2$, about $10^1$-$10^5$, about $10^1$-$10^6$, about $10^1$-$10^7$, about $10^2$-$10^8$, about $10^2$-$10^5$, about $10^2$-$10^6$, about $10^2$-$10^7$, about $10^5$-$10^8$, about $10^5$-$10^6$, or about $10^5$-$10^7$. In other embodiments, the strain rate is between about 0.1-10 s$^1$.

It will be appreciated that any or all of these approaches may be combined as appropriate.

In one embodiment, a microstructure assembly partially penetrates the skin with the first impact and the microstructure array detaches from the applicator or plunger.

A. Energy-Mass Applicator System

In one aspect, an applicator for delivery of a needle, microneedle, microprojection, microstructure, or arrays thereof is described herein. The applicator comprises an actuator or actuating member; a plunger element, at least a first and a second energy-mass element; and at least one needle, microneedle, microstructure, or arrays thereof capable of being retained or adhered to one of the plunger elements. The applicator operates by applying a force to the actuating member above a threshold to release the plunger elements and the energy-mass elements. The plunger and energy-mass elements provide multiple, discrete impacts with a single applicator. The applicator provides similar or even improved penetration of the microstructure(s) with less or no discomfort to the subject than is achieved with a single impact applicator.

Figure 2A:
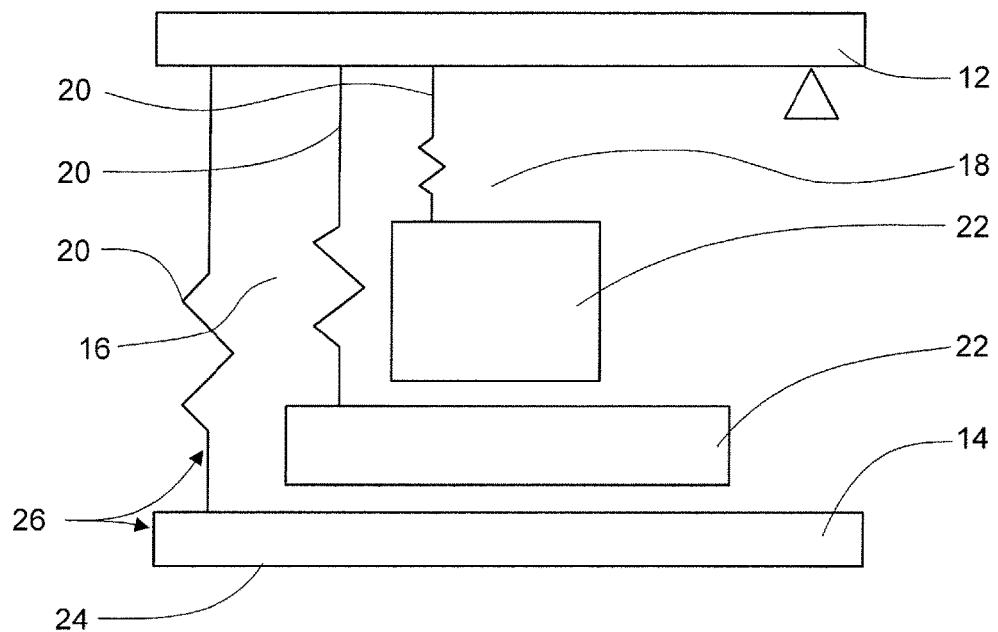
FIG. 2A is an illustration of a multiple energy-mass system for use in an applicator device in one embodiment.

The applicator 10 includes at least one plunger element, piston, or other elongate structure 14. The plunger element may have a central post or shaft, a proximal end or portion, and a distal end or portion. The shaft preferably extends between the distal ends or portions. It will be appreciated that the plunger may have any suitable size and/or shape. The applicator further comprises at least two energy-mass elements 16, 18, 26. In embodiments, the applicator comprises a plurality of energy-mass elements. In the embodiment as shown in FIG. 2, the applicator includes three energy-mass elements. It will be appreciated that the applicator may include at least about 2-5, about 2-3, about 2-4 or any number of energy-mass elements as necessary to achieve the desired penetration. It will be appreciated that having a greater number of energy-mass elements may reduce the force needed for the further impacts of the second and each additional energy-mass element. In the embodiment as shown in FIG. 2, the applicator includes a plunger 14 including a first energy-mass element 26 and two further energy-mass elements 16, 18. Each of the energy-mass elements includes an energy-storing element 20 and a mass 22. The second and third energy-mass elements 16, 18 are positioned such that they are constrained by the plunger and/or the plunger mass. The second and third energy-mass elements are further arranged in this embodiment such that their mass contacts the mass of the plunger to cause multiple impacts when the plunger and energy-mass elements are released.

The plunger element has a first constrained or restrained position and a second deployed or extended position. Further, each of the energy-mass elements has a first constrained or restrained position and a second deployed or extended position. The plunger elements and/or energy-mass elements may be retained or held in the constrained position by any suitable means. In an embodiment, the first plunger element is restrained in the first position and the second and third energy-mass elements (or further elements) are restrained by the first plunger element. In this embodiment, when the first plunger element is released from the constrained position, the second and third energy-mass elements are also released.

In one embodiment, the plunger includes at least one energy-mass element 26 effective to move the plunger from the first position to the second position when released. The energy-storing element is typically, but not always, positioned between the structure as described below and the mass element.

Figure 4A:
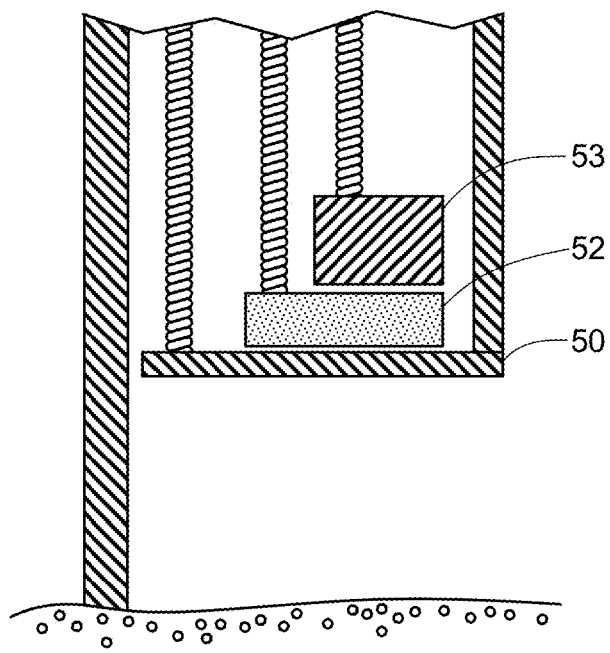
FIGS. 4A-4B are illustrations of a side view of an exemplary applicator device showing select features.
Figure 4B:
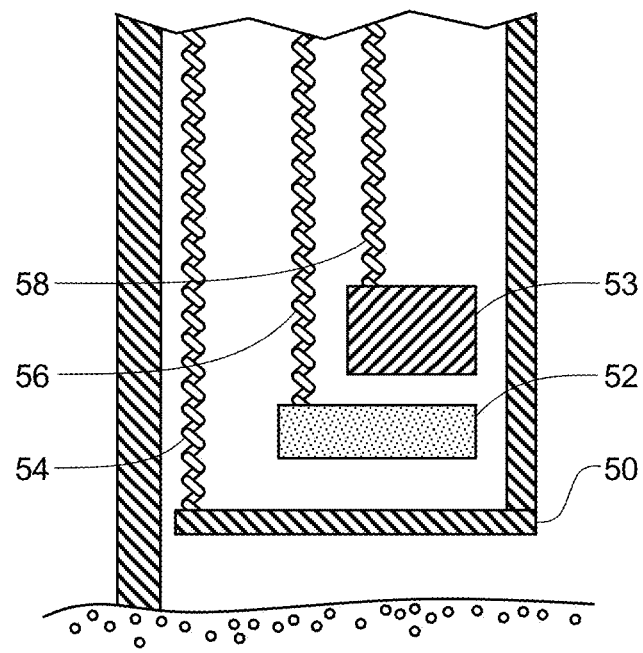

FIGS. 4A-4B show one embodiment of an energy-mass applicator in a constrained position (FIG. 4A) and in an extended position (at least partially) (FIG. 4B). An N-stage applicator can provide at least some of the benefits of vibration, which can improve penetration, with fewer parts and/or less complexity. In this embodiment, a first plunger element 50 is moved by a first spring or other energy storing element 54. Additional plunger elements 52, 53 are moved by a second and third spring or other energy storing element 56, 58, respectively. By selecting the mass of each of the plunger elements 50, 52, 53, the spring constants k1, k2, k3 for each of the springs 54, 56, 58 and the spring force lengths/compressions, one can ensure that the first plunger element 50 strikes the subject's skin first, followed by discrete strikes or impacts by further plunger elements 52, 53. It will be appreciated that any number of plunger elements and associated energy storing elements may be included in the applicator.

In one embodiment, this type of impactor/applicator should have user sensation comparable to a single-stage applicator using the maximum energy of any one of the multiple stages. The penetration, however, should be comparable to a single-stage applicator with energy equal to the sum of each of the multiple stages.

Any suitable energy-storing element is contemplated including, but not limited to springs or elastic components. In non-limiting embodiments, the energy-storing element is an elastic storage element, a compression spring, a coil spring, a wave spring, or a slotted spring device. When the plunger is in the restrained position, the energy-storage member is restrained in a high energy position of stored energy, and when the plunger is released, the energy-storage member releases its stored energy and in so doing moves the plunger. The energy storing element is typically maintained in a constrained or restrained position between a proximal surface of the plunger or the mass element and a distal surface of the structure described below. When the plunger is released, the energy storing element is released from the constrained position and the stored energy pushes the plunger distal end or mass element away from the common structure and toward the patient's skin. The amount of energy stored by the energy storing element may be adjusted based on the application area and/or microstructure structural features. The amount of stored energy may be, for example, in the range of at least about 0.1 J to at least about 10 J, or in the range of at least about 0.25 J to at least about 1 J. In other embodiments, the stored energy is in the range of at least about 0.15-0.25 J or at least about 0.15-0.2 J. In specific, but not limiting embodiments, the stored energy is at least about 0.15 J, about 0.2 J, about 0.25 J, or about 0.3 J. It will be appreciated that the energy-storage element may have sufficient stored energy for the first plunger distal end or mass to impact skin with a force of at least about 0.25 J to at least about 1 J. In other embodiments, the stored energy is in the range of at least about 0.15-0.25 J or at least about 0.15-0.2 J. In specific, but not limiting embodiments, the stored energy is at least about 0.15 J, about 0.2 J, about 0.25 J, or about 0.3 J. It will be appreciated that the energy stored by different energy-storing members may be different. For example, the energy-storing member of the first plunger element may have a greater stored energy than each of the second or further energy-storing elements. In other embodiments, each of the energy storing elements has the same or similar amount of stored energy. Preferably, the energy storing element of the first plunger element provides a sufficient energy for the microstructure or array on the plunger distal surface to pierce a subject's skin or other membrane surface. In an embodiment, the energy storing member is selected to provide a force on the plunger sufficient to cause the plunger to travel a distance longer than the length of the plunger shaft. In other embodiments including a housing discussed below, the energy storing member is selected to provide a force on the plunger sufficient to cause the plunger to travel a sufficient distance so that at least a portion of the plunger distal end exits the housing distal end.

In other embodiments, the energy-mass systems will typically accelerate at least the first plunger element to a velocity that is effective to pierce or rupture a patient's skin with the microstructure(s). In one embodiment, the maximum velocity of the microstructure(s) upon impact with the skin is about 20 meters per second (m/s) or less, about 15 m/s or less, about 10 m/s or less, about 8 m/s, about 6 m/s, about 4 m/s, or about 2 m/s. It will be appreciated that the maximum velocity for multiple impacts may vary among the impacts.

Preferably, the energy-mass elements or systems each have a different time constant such that the energy-mass elements deploy and/or impact the subject's skin at different times. In an embodiment, the first energy-mass element, associated with the plunger, has the fastest time constant such that the plunger impacts the subject's skin first based on the release of the first-energy mass system. In this embodiment, the plunger first impacts the skin with sufficient force for the microstructure(s) to rupture the skin or membrane surface and impacts from the second and/or further energy-mass elements cause increased penetration by the microstructure(s). Typically, the energy-mass systems are held by the plunger in a compressed state in decreasing order of time constant. Upon activation, the plunger and associated first energy-mass system moves fastest and separates from the other energy-mass systems. Each subsequent energy-mass system separates from the slower system behind it. The plunger impacts the subject's skin first based on release of the first energy-mass system, followed by impacts in order by each subsequent energy-mass system. Appropriate selection of energy-storing elements and masses can provide the desired time delay between impacts and total force.

As seen in FIG. 2, the energy-mass systems may be stacked or otherwise configured so that the slower masses impact the faster masses.

Increasing the number of impacts allows each individual impact to deliver less energy or force while achieving sufficient or desired penetration of the microstructure(s). Reducing the individual impact force of the plunger devices lowers the sensation caused by the applicator and allows for a reduction in sensation to the subject for the same microstructure penetration. Reducing the individual impact force also allows for an increase in penetration achieved with the same force.

In one embodiment, each of the plunger elements and/or energy-mass systems are attached, adhered, or otherwise connected to a common support or structure 12 that provides support to the plunger and/or energy-mass elements. The plunger elements and/or energy-mass elements may be retained by or secured to the structure by any suitable manner including, but not limited to, a mechanical feature such as a locking system, one or more fasteners, and/or an adhesive. In one embodiment, the structure is a plate. The structure may be any suitable size or shape to accommodate the plunger elements and/or systems. Where the apparatus includes a housing as described further below, the structure is preferably sized to fit within the housing. The structure may be flexible, rigid or substantially rigid. Preferably, the sufficient has sufficient mechanical strength and/or is sufficiently rigid to constrain, along with the plunger element, the energy-mass elements 16, 18, 26 as described more fully below.

As the actuator 60 is moved (e.g. from a first position to a second position), the actuator releases at least the plunger and/or first energy-mass element. It will be appreciated that the actuating member may have any shape or configuration that is suitable to allow the actuating member to push, move, or rotate to release at least the plunger and/or energy-mass element.

Pressure may be applied to move the actuating member from a first position to a second position by any suitable means including manual or mechanical. Where the pressure is manually applied, the actuating member has an external surface that is suitable for contact by a user or otherwise includes structure that allows a user to apply the appropriate pressure to the actuating member. In non-limiting embodiments, a force of at least about 0.5-10 lb is applied to the actuating member.

The bottom surface 24 of the plunger 14 further includes at least one needle, at least one microprojection, a microprojection array, a passive transdermal patch, or other delivery device for transdermal administration of one or more therapeutic agents. In an exemplary embodiment, at least one microprojection or a microprojection array is affixed, attached, adhered to, or integral with the bottom surface 24 of the plunger. In one embodiment, the delivery device is removably attached to the plunger distal surface. General features for microprojection arrays are described, for example, in U.S. Publication Nos. 2008/0269685, 2011/0276028, and U.S. Pat. Nos. 7,416,541, 7,578,954, 7,108,681, each of which are incorporated herein by reference. In embodiments, the microprojection is a hypodermic needle or a trocar. In further embodiments, the microprojection array comprises a plurality of microprojections, at least some of which are dissolvable or erodible microprojections. In further embodiments, at least some of the microprojections include at least one active agent, therapeutic agent, drug or other substance to be administered transdermally. Further, at least a portion of the microprojections may be detachable from the microprojection array. Detachable microprojection arrays are described in U.S. patent application No. 61/745,513, which is incorporated herein by reference.

In one non-limiting embodiment, the microprojection array or other delivery device is affixed or attached to the plunger distal end using an adhesive. Suitable adhesives include, but are not limited to, acrylic adhesives, acrylate adhesives, pressure sensitive adhesives, double-sided adhesive tape, double sided adhesive coated nonwoven or porous film, and UV curable adhesives. It will be appreciated that any medical device adhesive known in the art would be suitable. In another embodiment, at least a portion of the microstructure array or other delivery device is integral with at least a portion of the first plunger distal end.

The sizes of the microneedles and other protrusions for use with this invention will be a function of the manufacturing technology and of the precise application. In general, however, microneedles and other microprotrusions used in practice may be expected to have a length of about 20 to about 1000 microns, more preferably from about 50 to about 750 microns and most preferably from about 100 to about 500 microns. Often it will be desired that the microprotrusions will be long enough to penetrate at least partially through the stratum corneum layer of skin at some suitable point of application on the human body, for example the thigh, hip, arm, or torso.

The common structure and plunger may be formed of any suitable material. In one non-limiting embodiment, the common structure and plunger elements are at least partially formed of a material having an elastic modulus of between about 0.5-500 KSI. In an embodiment, at least one of the common structure and/or the plunger elements are formed of a metal including, but not limited to stainless steel, carbon steel, titanium, and alloys thereof.

As noted above, the applicator includes at least one energy-mass element or structure 16, 18, 26 positioned at least partially between a lower surface of the common structure and the distal end of the plunger element. As noted above, each of the energy-mass structures includes an energy-storing element or energy-storage member and at least one mass. A skilled artisan will appreciate the wide variety of energy-storing elements that would be suitable for use, and some examples are illustrated in U.S. Patent Publication No. 2011/0276027, which is incorporated herein by reference in its entirety. It is to be understood that other similar shapes, including but not limited to other axisymmetric shapes, may be used to create an energy-storing element. Further, non-symmetric shapes may be used to create an energy-storing element. It is also to be understood that the energy-storing element may comprise a plurality of individual energy-storing elements that may or may not be identical in size, shape, and material. The use of a plurality of individual energy-storage members may be useful to allow alteration of plunger velocity, energy, activation force, or other performance characteristics in ways that may not be achievable or different than with a single energy-storing element.

The material from which the energy-storing element is manufactured is variable, and a skilled artisan will appreciate that it is selected based on the several design considerations, including storage life and desired application force, which of course will also depend on the configuration of the member. Exemplary materials include metals, alloys, plastics, and specific examples include stainless steel and thermoplastics.

The velocity of the microprojection array or other delivery device at the time of contact with skin may be adjusted, for example, by varying the amount of stored energy in the energy-storing element and/or by changing the mass. In an embodiment, the mass in or of the plunger is varied or adjusted to adjust the velocity of the plunger. Varying the stored energy is done, for example, by controlling the energy-storing element's geometric design and the properties of the material(s) out of which the energy-storing element is made. The energy-storing element may have a compressed form in which the degree of compression (e.g., in one spatial direction) controls the amount of energy stored.

When the energy storing element is stored in a compressed form, a variety of mechanisms external to the element, but forming part of the applicator, may be employed to release the compression and allow the element to uncompress and therefore release some or all of its energy.

The applicator may further include an outer housing 28 at least partially surrounding or enclosing at least the plunger and/or energy-mass elements. Preferably at least part of the actuating member is accessible from the housing so that the user can apply pressure to the actuating member. It will be appreciated that at least a portion of the plunger extends beyond a distal end of the housing when released from its constrained or restrained position and/or at equilibrium so that the microprojection array or other delivery device is able to contact skin. It will also be appreciated that only a portion of the microstructures themselves need to extend beyond the housing distal end in order to penetrate skin. The distal end of the housing may include a skin contacting area or member 62 that is placed against a subject or patient's skin. The skin contacting area may be an annular ring positioned around an opening for the microprojection array or other delivery device. The skin contacting area may further include an adhesive for adhering the housing to the skin. The adhesive may be applied at least partially on the annular skin contacting area. In embodiments, the housing includes a surface on which an adhesive is or can be applied to secure the housing to a second surface. It will be appreciated that the skin contacting area may surround all or a portion of an opening for the microstructure array or other delivery device attached to the plunger distal end to pass through.

Applicators contemplated herein will commonly have at least two states or configurations. In the first state or configuration, the plunger is retained in a restrained or constrained position. In the first state or configuration, the energy-storing element is restrained between the common structure element and one of the plunger or an energy-mass element in a high energy position. This is typically expected to be the state of the applicator following manufacturing and during shipping and storage. When the plunger is released, the energy-storing element is released from the constrained state and releases all or a part of the stored energy. In this second state or configuration, which is arrived at by operating the actuating member or element, the microprojection array or other delivery device projects outward from the applicator.

The materials from which the applicator components are manufactured can be selected from a wide variety known to a skilled artisan. For example, a filled polymer material is suitable for manufacture of at least the outer cover or housing and/or the actuating member. A skilled artisan will understand the various material properties to be considered when selecting a suitable material for each component part.

B. Linear Energy-Mass and Torsional Energy-Mass Applicator

In another aspect, an applicator for delivery of a needle, microneedle, microprojection, microstructure, arrays thereof, or other delivery device is described herein. The applicator comprises an actuator or actuating member, at least one plunger or piston, a linear energy-mass system, and a torsional energy-mass system. The applicator operates by applying a force to the actuating member above a threshold to release the plunger.

Figure 3:
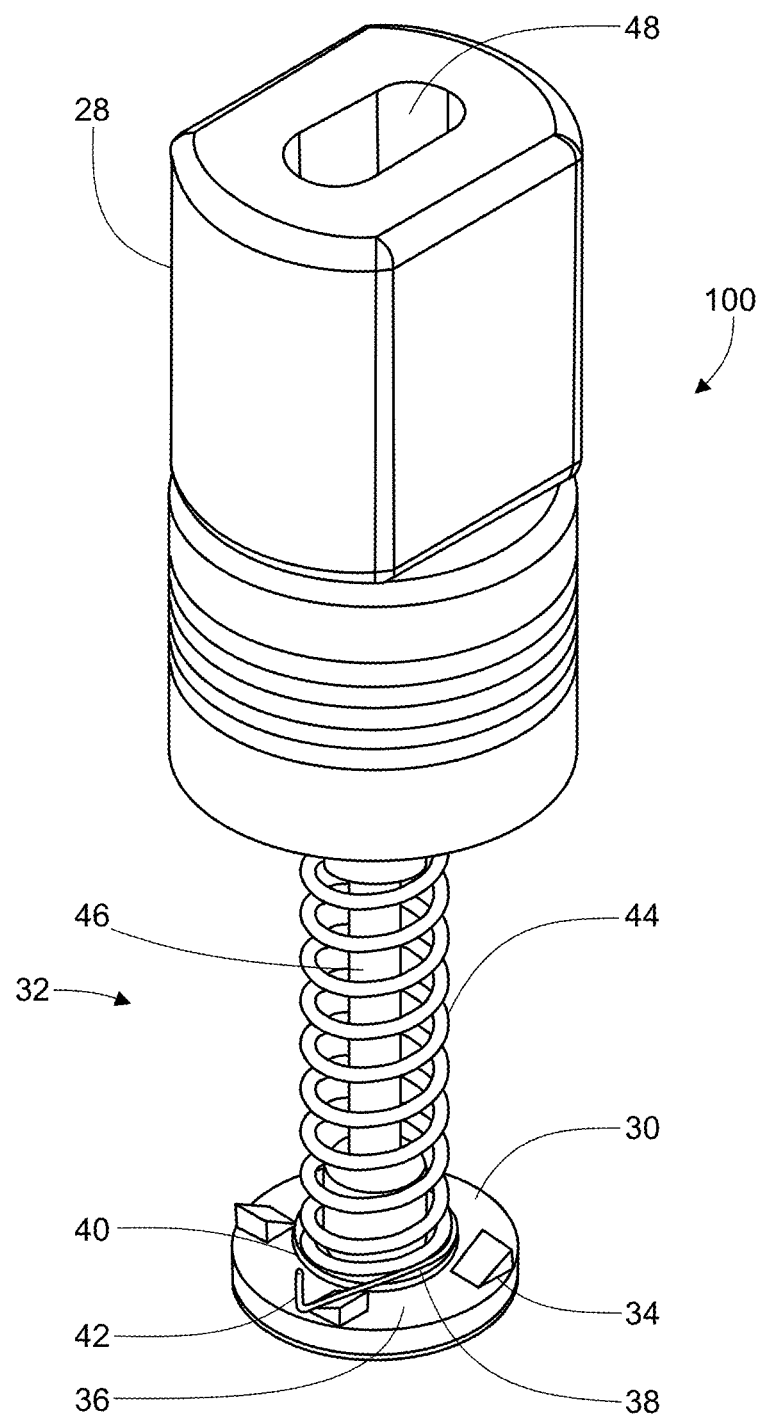
FIG. 3 is an illustration of a linear energy-mass system and a torsional energy-mass system for use in an exemplary applicator device.

FIG. 3 shows another exemplary actuator or applicator 100. As seen in FIG. 3, the applicator 100 comprises a linear energy-mass system 32 attached to a plunger or piston 30, and a torsional energy-mass system 38 with an axis of rotation collinear with the linear energy-mass axis of motion. In another embodiment, the torsional energy-mass system is capable of moving along an arcuate path at least partially around the plunger. In an embodiment, the torsional energy-mass system includes at least one torsional energy storage element 40 and at least one rod or other projection 42. In one embodiment, a proximal surface of the plunger distal end 36 includes one or more projections 34. The torsional energy-mass system rod 42 contacts the one or more projections as the torsional energy-mass system rotates about the plunger. Movement of the rod over the at least one projection causes the plunger distal end to move downward and impact the subject's skin.

Both the linear energy-mass system and the torsional energy-mass system are initially held in a compressed state. The linear energy-mass system and the torsional energy-mass system may be retained in the compressed state by any suitable means. The plunger and/or linear energy-mass system is released by action of an actuator, not shown, allowing the plunger distal end 36 to impact a subject's skin. The torsional energy-mass system is released and the attached rod or projection spins, rotates, or moves along an arcuate path around at least a portion of the plunger shaft 46. The rod contacts at least one of the projections(s) on the plunger distal end and the plunger distal end is pushed away from the rod providing a force in the axis of motion of the plunger toward the skin. The rod may be any suitable shape or length suitable to interact with the projections. In one embodiment, the torsional energy-mass system is released from its compressed state by impact of the plunger on the subject's skin.

In an embodiment, the plunger, piston or other elongate structure 30 has a central post or shaft 46 with a proximal end or portion and a distal end or portion 36. The shaft preferably extends at least partially between the proximal and distal ends or portions. It will be appreciated that the plunger may have any suitable shape or size. As shown at least in FIG. 3, one suitable shape comprises a cylindrical shaft with a circular or cylindrical distal end. In this particular embodiment, the distal end has a circular plate shape. It will be appreciated, however, that other shapes are suitable including, but not limited to, a rectangular prism or other polygonal prisms. It will further be appreciated that the shaft, proximal end, and distal end may each have a different geometry. As one example, the shaft and proximal end may be cylindrical with the distal end having a square or rectangular shape. It will further be appreciated that one or both of the proximal and distal ends may be a plate having a circular, square, rectangular, elliptical or irregular shape. In one embodiment, the proximal and/or distal end has a wider diameter than a diameter of the central shaft.

The plunger distal end further comprises at least one projection positioned on the proximal surface of the distal end. In embodiments, at least about 1-6 projections are positioned on the plunger distal end. In other embodiments, at least about 1-5, about 1-4, about 1-3, about 1-2, about 2-6, about 2-5, about 2-4, about 2-3, about 3-6, about 3-5, about 3-4, about 4-6, about 4-5, about 5-6 or more projections are positioned on the plunger distal end. In specific, but not limiting embodiments, at least about 1, 2, 3, 4, 5, or 6 projections are positioned on the plunger distal end. It will be appreciated that any number of projections corresponding to the number of impacts desired may be included on the plunger distal end. The projections may be any suitable size or shape as required to move the plunger distal end a suitable or desired distance. In the embodiment, the projections are wedge or ramp-shaped. Preferably, the projections are shaped such that the rod may travel at least partially over the projection in order to move the plunger distal end. In one embodiment, at least some of the projections have a ramp or incline for interaction with the rod. The projections may be integral with or otherwise attached to the plunger distal end. Where the projections are attached to the plunger distal end, they may be attached or affixed by any suitable means including, but not limited to mechanical means and/or an adhesive. The projections may be formed of any suitable material including, but not limited to, polymers and metals. The projections may be formed of the same or different materials as the plunger.

As seen in FIG. 3, the linear energy-mass system further includes an energy storing element 44 positioned between an upper or proximal surface of the plunger distal end and a lower or distal surface of a plate member; actuator, a portion of the housing, or other structure with sufficient mechanical strength to restrain or constrain the linear energy storing element 44. In another embodiment, the linear energy-storing element is retained by the plunger distal end and a plate or other structure positioned proximal to the plunger distal end. Any suitable energy-storing element is contemplated including, but not limited to springs or elastic components. The discussion of energy-storing elements above is relevant to and considered as part of the present embodiment. When the plunger is in the retained or constrained position, the linear energy-storing member is retained or constrained in a high energy position. When the plunger is released or deployed, the linear energy-storing member releases its stored energy and in so doing moves the plunger. The linear energy storing element is typically maintained in a constrained or restrained position between the proximal surface of the plunger or other structure and the proximal surface of the plunger distal end.

The applicator further includes a torsional energy-mass system comprising a torsional energy-storing element 40 and a rod or other projection 42. The torsional energy-storing element is initially held in a first constrained or restrained position. The torsional energy-storing element is released by the actuator, by release of the plunger, or other means and the rod moves in an arcuate path around at least a portion of the plunger. As the rod moves, it contacts the projections positioned on the plunger distal end. The rod moves at least partially over the projections and moves the plunger toward the patient's skin causing the plunger distal end to impact the skin one or more additional times. It will be appreciated that the impact depth is determined by the projection height and the impact duration is determined by the length of the projection. One skilled in the art may vary the size and shape of the projection in order to vary the impact dynamics including depth and duration. It will further be appreciated that the timing of the multiple impacts may be determined or controlled by the spacing between the projections and/or the speed of movement of the torsional energy-mass system.

The present embodiment may further include an outer housing 28 at least partially surrounding or enclosing the applicator. The discussion of a housing above is relevant to and included herein. Preferably at least part of the actuator is accessible or extends beyond the proximal end of the housing so that the user can apply pressure to the actuator. In another embodiment, the housing includes an actuator contacting area or element where the user applies pressure to the housing at the area or to the element that is transferred to the actuator proximal end. In another embodiment, the housing includes an opening 48 at the proximal end for a user to access the actuator. The actuator proximal end may extend at least partially through the opening in the housing or the opening may be dimensioned so that a user may access the proximal end of the actuator through the opening.

As with the above embodiment, applicators contemplated herein will commonly have at least two states or configurations. In the first state or configuration, the proximal end of the plunger is in its first retained or constrained position. In this first state or configuration, the linear energy-storing element and torsional energy-storing system are restrained in a high energy position. This is typically expected to be the state of the applicator following manufacturing and during shipping and storage. When the plunger moves from its first position to a second extended or deployed position, the linear energy-storing element is released from the constrained state and releases all or a part of the stored energy. In this second state or configuration of the linear energy storing element, which is arrived at by pressing or otherwise operating the actuating element, the microprojection array projects modestly outward from the applicator.

The applicators described in each of the embodiments described above can optionally include a safety mechanism or latch to prevent unintended actuation of the applicator and consequential deployment of the microneedle array. Various embodiments of a safety mechanism are described in U.S. Patent Publication No. 2011/0276027, which is incorporated herein in its entirety.

One problem with some prior applicators is the plunger is not deployed with sufficient energy or the plunger may bounce after contacting the skin or the skin may move away due to the impact. The skin may thus become separated from the microprotrusion array after the initial impact. Without a retaining force, the skin may separate at the end of the plunger's travel, continuing its motion as the plunger moves at a slower rate. While the microprotrusion array may later return to contact the skin as the plunger bounces, the individual microprotrusions will no longer be aligned with the holes created during the initial impact of the array with the skin and the plunger may not have sufficient energy to create new holes with the microprotrusions. Alternatively, some prior applicators suffer from the excessive application of force or displacement of the plunger. Excessive displacement or impact force of the plunger into the skin can cause uncomfortable sensations and/or pulling of the skin. Additionally, excessive compression of the skin can reduce fluid flow through the tissues surrounding the microprotrusion array, which slows dissolution of the therapeutic agent from the microprotrusions and the subsequent transport into the subject's system. Both of these problems may lead to the degradation of the drug product and/or improper or incomplete delivery of the therapeutic agent.

The proper contact of the microprotrusions with the skin may be achieved by adjusting the final equilibrium position of the plunger for any of the embodiments herein. In embodiments, the displacement of the plunger distal end is 0.03-0.2" below the surface of the subject's skin at equilibrium. In embodiments, the final displacement of the plunger of at least 0.030" as measured at plunger equilibrium in free air is desired. The "final displacement" refers to the extension of the plunger distal surface beyond the surface of the skin. This final displacement or the equilibrium position is determined by the length of the plunger and/or the equilibrium position of the linear energy-storage member. In other embodiments, a final displacement is approximately 0.2". In a specific embodiment, the final displacement is 0.2" using a spring with 54 lb/in and a plunger having a diameter of approximately 0.6". In an embodiment, the length of the plunger shaft is selected such that it extends beyond the distal most end of the housing at equilibrium. In another embodiment, the housing distal end includes a skin contacting surface and the length of the plunger shaft is selected such that the plunger extends beyond the skin contacting surface. In yet another embodiment, the plunger distal end extends below the skin surface at equilibrium. It will be appreciated the final displacement is dependent on the force required to depress the plunger from an extended state to flush with the housing. In an embodiment, the plunger travels a distance longer than the length of the plunger shaft. It will be appreciated that the length of the plunger shaft and/or the energy storing element may be selected to provide a force on the plunger that causes the plunger to travel a distance longer than the length of the shaft.

When the microprojections are dissolvable or erodible, a further advantage of an extended plunger equilibrium position is that the continued application of force allows the dissolvable microprojections to penetrate deeper into the skin as the microprojections dissolve. The biased force pressing the microprojections into the skin to the extended equilibrium position may further cause the microprojections to penetrate deeper into the skin as the distal tips dissolve.

Without being limited as to theory, maintaining pressure on the microprotrusions at equilibrium keeps the protrusion distal ends inserted in the skin. As the microprotrusions dissolve, the continued pressure pushes the protrusions deeper into the skin until the protrusions substantially or completely dissolve.

One problem with actuators using an energy-storing element such as a spring or elastic element is that the energy storage element may exert forces on one or more components of the applicators, leading to dimensional distortion and/or creep over an extended period of time. These effects are undesirable as they lead to variations in the applicator geometry and a loss in the stored elastic energy over time. In one embodiment, at least the upper retaining component or member and the plunger are formed of materials that do not exhibit creep. In one embodiment, at least the upper retaining component and plunger are formed from a metal. Exemplary metals include, but are not limited to stainless steel, carbon steel, titanium, and alloys thereof. In another embodiment, at least the upper retaining component and plunger are formed from a plastic or polymer that does not exhibit creep and/or dimensional distortion at a given stress level. In this embodiment, all of the mechanical load from the energy storage element is borne by parts formed from materials which are not subject to dimensional distortion and creep over time. Reducing the dimensional distortion and creep leads to maintaining the same stored elastic energy for an extended period of time. Maintaining the same stored elastic energy over a period of time is important for having an extended shelf life of at least preferably 6 months, more preferably 12 months, and most preferably 24 months. In further embodiments, the same stored elastic energy is maintained over a shelf life of at least about 1-10 years. In specific, but not limiting embodiments, the same stored elastic energy is maintained over a shelf life of at least about 1 year, about 2 years, about 3 years, about 4 years, about 5 years, or about 10 years or longer.

Another issue or problem with current microstructure or microneedle arrays arises with extended use or wear of the applicators. Wearing a potentially bulky applicator for an extended period of time is inconvenient during normal activities or exercising. Another potential problem is that the microneedle arrays may bounce off the skin and cause poor drug delivery. Furthermore, another potential problem is the microneedle array may pull out of the skin after impact into the skin also causing poor drug delivery. In some embodiments of each of the applicators described herein, it is desirable for the microstructure array or other delivery device to be removable from the applicator. This embodiment provides for a low profile and/or more comfortable delivery device that can be worn for longer or extended periods of time.

In one embodiment, any or all of the present applicators may include a backing assembly that is removable from the applicator. In one embodiment, a backing assembly may include a support layer, a microstructure array or other delivery device, and an adhesive positioned at least partially around the microstructure array or delivery device. In one embodiment, the adhesive is positioned as a ring around the microstructure array. The backing assembly is initially attached or placed in close proximity to the plunger or the applicator. Preferably, the backing assembly is attached or affixed to the distal surface of the plunger. Upon activation of the applicator, the plunger is released which deploys or forces the microstructures into the skin. The backing assembly with the adhesive ring at least partially adheres to the skin, allowing the applicator to detach from the skin with the microstructures of the array being deployed at least partially in the subject's skin. Another advantage of a backing assembly is that the microstructures are prevented from pulling out of the skin as the skin tissue relaxes for extended wear durations (e.g. ≤5 minutes). Additionally, this configuration prevents microstructures from pulling out due to the plunger bouncing off the skin after impact. The backing assembly preferably detaches from the plunger immediately after impact, and the adhesive ring on the backing assembly holds the microstructure array onto the skin. The plunger bounces upward and separates from the backing assembly or the backing assembly separates from the plunger when the applicator is removed. The backing assembly with the microstructure array stays on the skin. Any suitable adhesive for adhering the backing assembly may be used including those described with reference to the skin contacting area. In an embodiment, the adhesive has sufficient adhesion to the skin to retain the microstructure array on the subject's skin when the plunger bounces away from the skin or when the applicator is removed from the subject's skin. The support layer may be formed of any suitable material including, but not limited to, polymers and metals. In an embodiment, at least the areas of the support that contact the subject's skin are biocompatible. The support layer may be rigid, semi-rigid or flexible. In one embodiment, the support layer is flexible enough to conform to the skin application site. In an exemplary embodiment, the applicator with the plunger retained by the blocking member is first placed against a subject's skin. The backing assembly is positioned on the distalmost surface of the plunger distal end. The applicator is actuated and the blocking member releases the plunger, which is deployed downward toward the patient's skin. The microstructure array on the distal end of the plunger is deployed or driven such that at least a portion of the microstructures in the array at least partially pierce or penetrate the subject's skin. The plunger bounces or otherwise moves vertically away from the skin and the backing assembly detaches from the plunger to remain on the subject's skin.

Figure 2B:
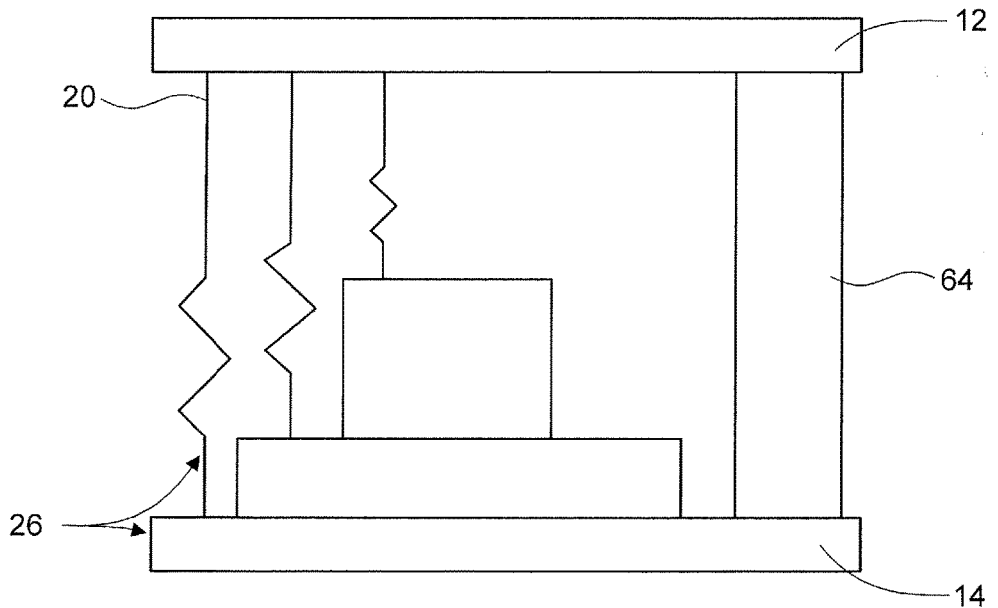
FIG. 2B is an illustration of a multiple energy-mass system for use in an applicator device including a damper in one embodiment.

In one embodiment, any or all of the applicators described herein may include a damper to dampen the bounce, upward or vertical motion away from a subject. The plunger damper changes the system dynamics from under-damped to critically or over-damped. In non-limiting embodiments, a foam, friction material, or viscous material is placed in mechanical communication with the plunger and the energy-storing element to act as a plunger damper. The plunger damper's function is to provide an energy loss to minimize plunger bounce (vertical upward motion) after the applicator is activated and the plunger strikes the skin. In one embodiment, the damper is positioned between the linear energy-storing device or other energy-storing device and the plunger distal end. When the plunger is released from its first position, the plunger deploys and the damper expands to at least partially fill any open space between the energy-storing device and the plunger distal end. FIG. 2B shows a multiple energy-mass system including a damper 64.

It will be appreciated that elements and/or embodiments described above with reference to one applicator embodiment are applicable to all applicator embodiments described. Discussion of common elements between the embodiments is intended to apply to all embodiments. In particular, but without limitation, discussion of the actuating member, plunger, delivery devices, energy-storage elements, and housing with reference to one embodiment is intended to also apply to other embodiments.

III. Methods Of Use

In another aspect, a method for administering an active agent or therapeutic agent to a subject is provided. Preferably, the active or therapeutic agent is administered dermally, transdermally, mucosally, and/or transmucosally. The method comprises providing a microprojection array or other delivery device in conjunction with any one of the applicators described herein, the microprojection array or delivery device comprising at least one active agent. Preferably, the microprojection array or other delivery device is configured to deliver at least one therapeutic agent. The agent may be coated on at least a portion of the microprojections and/or contained within at least a portion of the microstructures. The agent is delivered dermally, transdermally, mucosally, or transmucosally by actuation of the applicator, to deploy the microprojection array into contact with the skin, or more generally a membrane or body surface, of a subject. The active agent to be administered can be one or more of any of the active agents known in the art, and include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof. In embodiments the therapeutic agent is a protein or a peptide. In another embodiment, the agent is a vaccine.

Non-limiting examples of peptides and proteins which may be used with microprotrusion arrays include, but are not limited to parathyroid hormone (PTH), oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides is also contemplated, and includes DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

In other embodiments, at least a portion of the distal layer comprises an agent suitable for use as a prophylactic and/or therapeutic vaccine. In an embodiment, the vaccine comprises an antigen epitope conjugated on or to a carrier protein. It will be appreciated that vaccines may be formulated with our without an adjuvant. Suitable vaccines include, but are not limited to, vaccines for use against anthrax, diphtheria/tetanus/pertussis, hepatitis A, hepatitis B, Haemophilus influenzae type b, human papillomavirus, influenza, Japanese encephalitis, measles/mumps/rubella, meningococcal diseases (e.g., meningococcal polysaccharide vaccine and meningococcal conjugate vaccine), pneumococcal diseases (e.g., pneumococcal polysaccharide vaccine and meningococcal conjugate vaccine), polio, rabies, rotavirus, shingles, smallpox, tetanus/diphtheria, tetanus/diphtheria/pertussis, typhoid, varicella, and yellow fever.

In another embodiment, at least a portion of the distal layer comprises an agent suitable for veterinary uses. Such uses include, but are not limited to, therapeutic and diagnostic veterinary uses.

As dosage requirements increase, the penetrated volume of microstructure arrays (MSA) also increases to accommodate the increased dose. The energy required to penetrate the increased volume also increases as a consequence. Increased energy for delivery of a MSA can cause increased, higher or undesirable sensations to the patient or even pain. Generally, an applicator is placed in contact with the skin such that a skin contacting surface directly contacts the external skin surface and, optionally, is adhered or affixed to the skin. A MSA is applied to the skin using a velocity that is at least or greater than a minimum velocity required for the microstructures to rupture or pierce the skin surface. With the MSA remaining in the skin, the MSA is impacted multiple, or at least one, times with a lower force. Since the MSA has already ruptured the skin surface, there is no minimum energy requirement for subsequent impacts. The MSA is impacted multiple times or until the sum of the energy of impacts is greater than or equal to the energy requirement for the MSA to penetrate a desired amount or volume. This approach spreads the energy required to achieve a desired volume penetration over time, which reduces the strain rate and keeps the strain small by keeping the energy quanta small.

In a first aspect of operation, an applicator comprising a plurality of energy-mass elements is placed in contact with a subject's skin such that a skin contacting surface of the applicator directly contacts the external skin surface (stratum corneum) and, optionally, is adhered to skin by means of adhesive disposed on the skin contacting surface. The plunger and each of the energy-mass elements are in a first, constrained state or position and are movable to a second extended or unrestrained state or configuration. Each of the energy-mass elements has a different time constant. The actuating member is pressed downward or otherwise moved causing release of the plunger from its first position. Release of the plunger from its first position also releases the energy-mass elements allowing the energy-storing elements to travel from the restrained or compressed position to an extended position. The plunger distal end is moved initially by the first energy-mass element and a microarray in contact with the plunger distal end comes forcibly into contact with skin. The second energy-mass element contacts at least a portion of the plunger according to its time constant. Contact of the second energy-mass element moves the plunger in a direction toward the subject's skin resulting in multiple impacts. The timing of the impacts may be determined or controlled by adjusting the time constant of the energy-mass elements. In one embodiment, the plunger after release has an equilibrium position such that the distal end of the plunger on which the microprotrusion array is affixed is positioned below a surface of the skin.

In a second aspect of operation, an applicator comprising a linear energy-mass element, a torsional energy-mass element, and a plunger is placed in contact with the skin such that a skin contacting surface of the applicator directly contacts the external skin surface (stratum corneum) and, optionally, is adhered to skin by means of adhesive disposed on the skin contacting surface. The plunger and each of the energy-mass elements are in a first, constrained state or position and are movable to a second extended or unrestrained state or configuration. The actuating member is pressed downward or otherwise moved causing release of the plunger from its first position. Release of the plunger from its first position also releases the linear energy-mass element allowing the linear energy-storing element to travel from the restrained or compressed position to an extended position. The plunger distal end is moved by the linear energy-mass element and a microarray in contact with the plunger distal end comes forcibly into contact with skin. The torsional energy-mass element is released and the torsional energy-storing element moves in an arcuate direction around at least a portion of the plunger shaft. In one embodiment, the torsional energy storage element is released upon initial contact or impact of the plunger distal end with the subject's skin. A rod travels perpendicular to the linear energy-mass axis of motion and around at least a portion of the plunger shaft and contacts at least one or more projections formed on or attached to the proximal surface of the plunger distal surface. Contact of the rod with each of the projections moves the plunger in a direction toward the subject's skin resulting in multiple impacts. The timing of the impacts may be determined or controlled by adjusting the spacing and shape of the projections. In one embodiment, the plunger after release has an equilibrium position such that the distal end of the plunger on which the microprotrusion array is affixed is positioned below a surface of the skin.

IV. Examples

The following examples are illustrative in nature and are in no way intended to be limiting. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

Administration of a Microstructure Array

A standard applicator comprising a microstructure array is applied to a subject's skin and the skin was impacted 1, 2, or 3 times with an energy quanta of 0.2 J. Multiple impacts increase the penetrated volume.

1. A method of delivering a therapeutic agent to a subject, comprising:
    applying to a skin site of a subject, an applicator comprising at least one plunger element, at least one microprojection retained on a distal surface of the plunger, and an actuator;
    actuating the actuator to convey an external force to the at least one plunger element such that an energy required for the at least one microprojection to penetrate the skin site is delivered in multiple, discrete quanta and/or impacts.
2. The method of embodiment 1, wherein a maximum strain and/or strain rate is not exceeded by any of the multiple, discrete quanta and/or impacts.
3. The method of the combined or separate embodiments 1-2, wherein there is sufficient delay between impacts to allow a strain from a previous impact to dissipate.
4. The method of the combined or separate embodiments 1-,3 wherein the at least one microstructure partially penetrates the skin site from a first impact, further comprising:
    detaching the at least one microstructure from the plunger distal end.
5. The method of the combined or separate embodiments 1-4, wherein, the multiple, discrete quanta and/or impacts are created by one or more of:
    (a) the plunger comprises multiple energy-mass systems, each system having a different time constant;
    (b) the applicator comprises a plurality of plunger elements and an asynchronous release mechanism such that the plunger elements are released at different time periods;
    (c) the applicator comprises a plurality of plunger elements each comprising a dashpot element having a different damping coefficient;
    (d) the applicator comprises a plurality of plunger elements, each having a different type of spring; and
    (e) the applicator further includes a vibration element.
6. The method of the combined or separate embodiments 1-5, wherein the each of the energy-mass systems has a progressively higher time constant such that the plunger elements impact the skin site in a defined sequence.
7. The method of the combined or separate embodiments 1-6, wherein each energy-mass element includes a spring and a mass element.
8. The method of the combined or separate embodiments 1-7, wherein a delay in impact from the plunger elements may be modified by adjusting a spring constant of one or more springs in the energy-mass elements.
9. The method of the combined or separate embodiments 1-8, wherein a delay in impact from the plunger elements may be modified by adjusting a mass of the mass elements.
10. The method of the combined or separate embodiments 1-9, further comprising a cam to provide the asynchronous release.
11. The method of the combined or separate embodiments 1-10, wherein the different types of springs are selected from coiled springs, wave springs, and slotted springs.
12. The method of the combined or separate embodiments 1-11, wherein an amplitude of the vibration element is controlled to limit an impact strain from one or more of the multiple, discrete quanta and/or impacts.
13. The method of the combined or separate embodiments 1-12, wherein a frequency of the vibration element is controlled to limit an impact strain from one or more of the multiple, discrete quanta and/or impacts.
14. An applicator, comprising:
    at least a first plunger element comprising a first energy-mass system, the first plunger element having a first restrained position and a second extended position, the first plunger element comprising a distal end on which at least one microprojection can be retained;
    at least a second energy-mass system, wherein the first and second energy-mass systems each has a different time constant, and each energy-mass system has a first restrained position and a second extended position; and
    an actuating member that can convey an external force to at least the first plunger element to release the first plunger element from the first restrained position.
15. The applicator of embodiment 14, further comprising at least one microstructure attached to a distal surface of the plunger element distal end.
16. The applicator of the combined or separate embodiments 14-15, wherein the first and second energy-mass systems each includes a mass and an energy-storing element.
17. The applicator of the combined or separate embodiments 14-16, wherein the energy-storing elements are elastic energy elements.
18. The applicator of the combined or separate embodiments 14-17, wherein the energy-storing elements are each selected from a compression spring, a coil spring, a wave spring, and a slotted spring.
19. The applicator of the combined or separate embodiments 14-18, wherein the first energy-mass system has a faster time constant than the second energy-mass system.
20. The applicator of the combined or separate embodiments 14-19, wherein the mass of the first energy-mass system is different than the mass of the second energy-mass system.
21. The applicator of the combined or separate embodiments 14-20, wherein the first energy-mass system has a stored energy sufficient to deploy the at least one microprojection at least partially into a subject's skin when the stored energy is released.
22. The applicator of the combined or separate embodiments 14-21, further comprising a third energy-mass system, wherein the third energy-mass system has a different time constant than the first or second energy-mass systems.
23. The applicator of the combined or separate embodiments 14-22, wherein the third energy-mass system has a slower time constant than the first or second energy-mass systems.
24. The applicator of the combined or separate embodiments 14-23, further comprising a housing member at least partially housing the first plunger element and actuating member.
25. The applicator of the combined or separate embodiments 14-24, wherein the housing member includes a skin-contacting surface.
26. The applicator of the combined or separate embodiments 14-25, the skin-contacting surface further comprising an adhesive to secure the housing to a surface.
27. The applicator of the combined or separate embodiments 14-26, wherein the at least one microprojection is a microprojection array comprising a plurality of microprojections.
28. The applicator of the combined or separate embodiments 14-27, wherein at least some of the plurality of microprojections are dissolvable or erodible microprojections.
29. The applicator of the combined or separate embodiments 14-28, wherein at least some of the plurality of microprojections include at least one therapeutic agent.

30. The applicator of the combined or separate embodiments 14-29, wherein the therapeutic agent is selected from a drug, a small molecule, a peptide or protein, or a vaccine.

31. The applicator of the combined or separate embodiments 14-30, wherein at least a portion of the plurality of microprojections are detachable from the microprojection array.

32. The applicator of the combined or separate embodiments 14-31, where the first plunger element contacts a subject's skin with an energy of about 0.15-0.2 J.

33. The applicator of the combined or separate embodiments 14-32, further comprising:
a backing member positioned on the distal surface of the first plunger distal end, wherein the backing member comprises the at least one microprojection;
the backing member being detachable from the first plunger element distal end.

34. The applicator of the combined or separate embodiments 14-33, wherein the backing member comprises a support layer adjacent the distal surface of the first plunger element distal end and an adhesive layer, wherein the at least one microprojection is positioned distal to the adhesive layer.

35. The applicator of the combined or separate embodiments 14-34, wherein the at least one microprojection is a microprojection array positioned distal to the adhesive layer.

36. The applicator of the combined or separate embodiments 14-35, wherein the adhesive layer at least partially surrounds the at least one microprojection.

37. The applicator of the combined or separate embodiments 14-36, further comprising:
a damper positioned between at least one of the energy-storing elements and a proximal surface of the first plunger element distal end.

38. A method of delivering a therapeutic agent to a subject, comprising:
applying to a skin site of the subject, an applicator according to any one of the combined or separate embodiments 1-37;
actuating the actuating member to convey an external force to at least the first plunger element;
releasing the first plunger element from the first restrained position to the second extended position to impact the subject's skin;
releasing the second energy-mass system from the first restrained position to the second extended position with a different time constant than the first plunger element;
wherein the second energy mass system impacts a proximal surface of the first plunger distal end.

39. The method of embodiment 38, wherein the first plunger contacts the skin site of the subject with sufficient force for the at least one microprojection to at least partially penetrate the skin.

40. The method of the combined or separate embodiments 38-39, wherein impact of the second energy-mass system on the first plunger element causes the at least one microprojection to penetrate the skin further upon impact.

41. The method of the combined or separate embodiments 38-40, further comprising:
adhering the applicator to the subject's skin.

42. The method of the combined or separate embodiments 38-41, wherein in the deployed position, the first plunger element has an equilibrium position such that the distal end of the plunger on which the at least one microprojection is retained is positioned below a surface of the skin.

43. The method of the combined or separate embodiments 38-42, wherein the equilibrium position is about 0.03-0.2 inches below the surface of the skin of the subject.

44. The method of the combined or separate embodiments 38-43, further comprising:
detaching a backing member such that the backing member and the at least one microprojection are retained on the subject's skin.

45. The method of the combined or separate embodiments 38-44, herein the therapeutic agent is selected from a drug, a small molecule, a peptide or protein, or a vaccine.

46. An applicator, comprising:
a plunger element comprising at least a shaft and a distal end on which at least one microprojection can be retained;
at least one projection positioned on a proximal surface of the plunger distal end, the plunger having a first restrained position and a second extended position;
an actuating member that can convey an external force to the plunger element to release the plunger element from the first restrained position;
a linear energy-storing member positioned between the actuator and the plunger distal end, the linear energy-storing member having a first position and a second position, wherein the linear energy-storing member is effective to move the plunger from its first position to its second position as the linear energy-storing member moves from its first position to its second position; and
a torsional energy-mass system at least partially surrounding the plunger shaft and being positioned between the linear energy-storing member and the plunger distal end, wherein the torsional energy-mass system contacts the at least one projection as the torsional energy-mass system rotates about the plunger shaft.

47. The applicator of embodiment 45, wherein the at least one projection comprises a plurality of projections spaced apart around the proximal surface of the plunger distal end.

48. The applicator of the combined or separate embodiments 46-47, wherein the torsional energy-mass system contacts the at least one projection as the torsional energy-mass system rotates about the plunger shaft and pushes the plunger distal end downward.

49. The applicator of the combined or separate embodiments 46-48 wherein the torsional energy-mass system includes a rod perpendicular to an axis of motion of the linear energy-storing member, wherein the rod contacts the at least one projection as the torsional energy-mass system rotates.

50. The applicator of the combined or separate embodiments 46-49, wherein impact of the plunger distal end on a patient's skin releases the torsional spring-mass system.

51. The applicator of the combined or separate embodiments 46-50, each of the at least one protrusions are wedge shaped.

52. The applicator of the combined or separate embodiments 46-51, wherein the energy-storing member is an elastic energy element.

53. The applicator of the combined or separate embodiments 46-52, wherein the energy-storing elements are each selected from a compression spring, a coil spring, and a wave spring.

54. The applicator of the combined or separate embodiments 46-53, wherein the linear energy-storing member has a stored energy sufficient to deploy the at least one microprojection into a subject's skin when the stored energy is released.

55. The applicator of the combined or separate embodiments 46-54, further comprising a housing member at least partially housing the plunger member and actuating member.
56. The applicator of the combined or separate embodiments 46-55, wherein the housing member includes a skin-contacting surface.
57. The applicator of the combined or separate embodiments 46-56, the skin-contacting surface further comprising an adhesive to secure the housing to a surface.
58. The applicator of the combined or separate embodiments 46-57, wherein the at least one microprojection is a microprojection array comprising a plurality of microprojections.
59. The applicator of the combined or separate embodiments 46-58, wherein at least some of the plurality of microprojections are dissolvable or erodible microprojections.
60. The applicator of the combined or separate embodiments 46-59, wherein the plurality of microprojections include at least one therapeutic agent.
61. The applicator of the combined or separate embodiments 46-60, wherein the therapeutic agent is selected from a drug, a small molecule, a peptide or protein, or a vaccine.
62. The applicator of the combined or separate embodiments 46-61, wherein at least a portion of the plurality of microprojections are detachable from the microprojection array.
63. The applicator of the combined or separate embodiments 46-62, where the plunger element contacts a subject's skin with a force of about 0.15-0.2 J.
64. The applicator of the combined or separate embodiments 46-63, further comprising:
a backing member positioned on a bottom surface of the plunger distal end, wherein the backing member comprises the at least one microprojection;
the backing member being detachable from the plunger distal end.
65. The applicator of the combined or separate embodiments 46-, wherein the backing member comprises a support layer adjacent the distal surface of the plunger distal end and an adhesive layer, wherein the at least one microprojection is positioned distal to the adhesive layer.
66. The applicator of the combined or separate embodiments 46-65, wherein the at least one microprojection is a microprojection array positioned distal to the adhesive layer.
67. The applicator of the combined or separate embodiments 46-66, wherein the adhesive layer at least partially surrounds the at least one microprojection.
68. The applicator of the combined or separate embodiments 46-67, further comprising:
a damper positioned between the energy-storage devices and a proximal surface of the plunger distal end.
69. A method of delivering a therapeutic agent to a subject, comprising:
applying to a skin site of the subject, an applicator according to the combined or separate embodiments 46-68;
actuating the actuating member to convey an external force to the plunger element;
releasing the plunger element from the first restrained position to the second extended position;
rotating the torsional energy-mass system about the plunger shaft such that the system contacts the at least one projection on the plunger proximal surface and pushes it downward as the system rotates about the plunger shaft thereby to move the plunger distal end toward the skin site.
70. The method of embodiment 69, wherein the plunger contacts the skin site of the subject in the extended position with sufficient force for the at least one microprojection to at least partially penetrate the skin.
71. The method of the combined or separate embodiments 69-70, wherein rotation of the torsional energy-mass system causes the plunger to impact the patient's skin and causes the at least one microprojection to penetrate the skin further upon each impact.
72. The method of the combined or separate embodiments 69-71, wherein the plunger distal end comprises a plurality of projections spaced apart around the proximal surface of the plunger distal end and rotation of the torsional energy-mass system causes the plunger to impact the patient's skin each time the system contacts one of the plurality of projections.
73. The method of the combined or separate embodiments 69-72, further comprising:
adhering the applicator to the subject's skin.
74. The method of the combined or separate embodiments 69-73, wherein in the deployed position, the plunger element has an equilibrium position such that the distal end of the plunger on which the at least one microprojection is retained is positioned below a surface of the skin.
75. The method of the combined or separate embodiments 69-74, wherein the equilibrium position is about 0.03-0.2 inches below the surface of the skin of the subject.
76. The method of the combined or separate embodiments 69-75, further comprising:
detaching a backing member such that the backing member and the at least one microprotrusion is retained on the subject's skin.
77. The method of the combined or separate embodiments 69-76, wherein the therapeutic agent is selected from a drug, a small molecule, a peptide or protein, or a vaccine.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:
1. A method of delivering a therapeutic agent to a subject, comprising:
applying to a skin site of a subject, an applicator comprising at least one plunger element, at least one microprojection retained on a distal surface of the plunger, and an actuator;
actuating the actuator to convey an external force to the at least one plunger element such that an energy required for the at least one microprojection to penetrate the skin site is delivered in multiple, discrete quanta and/or impacts at the skin site;

wherein, the multiple, discrete quanta and/or impacts are created by at least
the plunger comprising multiple energy-mass systems, each system having a different time constant, wherein each of the energy-mass systems has a progressively higher time constant such that the plunger elements impact the skin site in a defined sequence.

2. The method of claim 1, wherein a maximum strain and/or strain rate is not exceeded by any of the multiple, discrete quanta and/or impacts.

3. The method of claim 1, further comprising delaying between impacts at the skin site a sufficient time to allow a strain from a previous impact at the skin site to dissipate.

4. The method of claim 1, wherein the at least one microprojection partially penetrates the skin site from a first impact, further comprising:
detaching the at least one microprojection from the plunger distal end.

5. The method of claim 1, wherein each energy-mass system includes a spring and a mass element, further comprising
adjusting a spring constant of one or more springs in the energy-mass systems to modify a delay in impact from the plunger elements.

6. The method of claim 5, further comprising:
adjusting a mass of the mass elements thereby to modify a delay in impact from the plunger elements.

7. The method of claim 1, further comprising:
wherein the applicator further includes a vibration element and controlling an amplitude of the vibration element to limit an impact strain from one or more of the multiple, discrete quanta and/or impacts.

8. The method of claim 1, further comprising:
wherein the applicator further includes a vibration element and controlling a frequency of the vibration element to limit an impact strain from one or more of the multiple, discrete quanta and/or impacts.

9. The method of claim 1, wherein the at least one plunger element contacts a subject's skin with an energy of about 0.15-0.2 J.

10. The method of claim 1, wherein the multiple, discrete quanta and/or impacts are further created by the applicator comprising a plurality of plunger elements and an asynchronous release mechanism such that the plunger elements are released at different time periods.

11. The method of claim 1, wherein the multiple, discrete quanta and/or impacts are further created by the applicator comprising a plurality of plunger elements each comprising a dashpot element having a different damping coefficient.

12. The method of claim 1, wherein the multiple, discrete quanta and/or impacts are further created by the applicator comprising a plurality of plunger elements, each having a different type of spring.

13. An applicator, comprising:
at least a first plunger element comprising a first energy-mass system, the first plunger element having a first restrained position and a second extended position, the first plunger element comprising a distal end on which at least one microprojection can be retained;
at least a second energy-mass system;
wherein the first and second energy-mass systems each has a different time constant, and each energy-mass system has a first restrained position and a second extended position;
an actuating member that can convey an external force to at least the first plunger element to release the first plunger element from the first restrained position; and
at least one microprojection attached to a distal surface of the plunger element distal end;
wherein the first energy-mass system has a faster time constant than the second energy-mass system such that the energy required for the at least one microprojection to penetrate a subject's skin at an application site is delivered by multiple, discrete impacts at the skin by the first and second energy-mass systems.

14. The applicator of claim 13, wherein the first and second energy-mass systems each includes a mass and an energy-storing element.

15. The applicator of claim 14, wherein the energy-storing elements are elastic energy elements each selected from a compression spring, a coil spring, a wave spring, and a slotted spring.

16. The applicator of claim 14, wherein the mass of the first energy-mass system is different than the mass of the second energy-mass system.

17. The applicator of claim 13, further comprising a third energy-mass system, wherein the third energy-mass system has a different time constant than the first or second energy-mass systems.

18. The applicator of claim 17, wherein the third energy-mass system has a slower time constant than the first or second energy-mass systems.

19. The applicator of claim 13, further comprising a housing member at least partially housing the first plunger element and actuating member.

20. The applicator of claim 13, wherein the at least one microprojection is a microprojection array comprising a plurality of microprojections.

21. The applicator of claim 20, wherein at least some of the plurality of microprojections are dissolvable or erodible microprojections.

22. The applicator of claim 20, wherein at least some of the plurality of microprojections include at least one therapeutic agent selected from a drug, a small molecule, a peptide or protein, or a vaccine.

23. The applicator of claim 20, wherein at least a portion of the plurality of microprojections are detachable from the microprojection array.

24. The applicator of claim 12, further comprising:
a damper positioned between at least one of the energy-storing elements and a proximal surface of the first plunger element distal end.

* * * * *